(12) United States Patent
Soong et al.

(10) Patent No.: US 8,227,221 B2
(45) Date of Patent: Jul. 24, 2012

(54) PROCESSES OF PRODUCING FERMENTATION PRODUCTS

(75) Inventors: Chee-Leong Soong, Raleigh, NC (US);
Jiyin Liu, Raleigh, NC (US);
Zhengfang Kang, Raleigh, NC (US)

(73) Assignee: Novozymes North America, Inc., Franklinton, NC (US)

( * ) Notice: Subject to any disclaimer, the term of this patent is extended or adjusted under 35 U.S.C. 154(b) by 254 days.

(21) Appl. No.: 12/743,377

(22) PCT Filed: Nov. 19, 2008

(86) PCT No.: PCT/US2008/083963
§ 371 (c)(1),
(2), (4) Date: May 18, 2010

(87) PCT Pub. No.: WO2009/067471
PCT Pub. Date: May 28, 2009

(65) Prior Publication Data
US 2010/0279371 A1    Nov. 4, 2010

Related U.S. Application Data

(60) Provisional application No. 60/988,873, filed on Nov. 19, 2007.

(51) Int. Cl.
*C12P 7/06*   (2006.01)
*C12P 7/10*   (2006.01)
*C12P 1/04*   (2006.01)
*C12P 1/02*   (2006.01)
*C12Q 1/42*   (2006.01)
*C12Q 1/54*   (2006.01)
*C12P 1/00*   (2006.01)
*C12P 7/08*   (2006.01)

(52) U.S. Cl. .............. 435/161; 435/14; 435/21; 435/41; 435/163; 435/165; 435/170; 435/171

(58) Field of Classification Search .................. 435/14, 435/18, 21, 22, 161, 163, 165, 170, 171
See application file for complete search history.

(56) References Cited

U.S. PATENT DOCUMENTS

2002/0006647 A1 * 1/2002 Veit et al. .................. 435/162

FOREIGN PATENT DOCUMENTS

WO    WO 83/02952    9/1983

OTHER PUBLICATIONS

Lopes, D.H.J. et al. 1999. Effects of Trehalose and Ethanol on Yeast Cytosolic Pyrophosphatase. , Z. Naturforsch. , vol. 54 c, pp. 186-190.*
Raugei et al., "Expression of acyiphosphatase in *Saccharomyces cerevisiae* enhances ethanol termentation rate"Biotechnology and Applied Biochemistry, vol. 23, No. 3, pp. 273-278 (1996).
Perez-Castineira et al., "Functional complementation of yeast cytosotic pryrophosphatase by bacterial and plant H+-translocating pyrophophatases", Proceedings of the National Academy of Sciences of the USA, vol. 99, No. 25, pp. 15914-15919 (2002).
Grazinoli-Garrido et al., "Inactivation of yeast inorganic pyrophosphatase by organic solvents", Anais de Academia Brasiteira de Olencias, vol. 76, No. 4. pp. 699-705 (2004).
Du Jardin et al., "Molecular cloning and characterization of a soluble inorganic pyrophosphatase in potato", Plant Physiology, vol. 109, No. 3, pp. 853-860 (1995).
Lopes et al., "Urea increases tolerance of yeast inorganic pryrophosphatase activity to ethanol: the other side of urea interaction with proteins", Archives of Biochemistry and Biophysics, vol. 394, No. 1, pp. 61-66 (2001).
Search Report issued in corresponding International application No. PCT/US2008/083963 dated May 12, 2009.

* cited by examiner

*Primary Examiner* — Jon P Weber
*Assistant Examiner* — Kailash C Srivastava
(74) *Attorney, Agent, or Firm* — Elias Lambiris

(57) ABSTRACT

The invention relates to a process of fermenting plant material in a fermentation medium into a fermentation product using a fermenting organism, wherein increased levels of one or more pyrophosphatase enzymes are present in the fermentation medium.

17 Claims, 6 Drawing Sheets

US 8,227,221 B2

PROCESSES OF PRODUCING FERMENTATION PRODUCTS

CROSS-REFERENCE TO RELATED APPLICATIONS

This application is a 35 U.S.C. 371 national application of PCT/US2008/083963 filed Nov. 19, 2008, which claims priority or the benefit under 35 U.S.C. 119 of U.S. provisional application no. 60/988,873 filed Nov. 19, 2007, the contents of which are fully incorporated herein by reference.

TECHNICAL FIELD

The present invention relates to processes of fermenting plant material into desired fermentation products. The invention also relates to processes of producing a fermentation product from plant material using one or more fermenting organisms and to compositions that can be used in such processes.

BACKGROUND ART

A vast number of commercial products that are difficult to produce synthetically are today produced by fermenting organisms. Such products including alcohols (e.g., ethanol, methanol, butanol, 1,3-propanediol); organic acids (e.g., citric acid, acetic acid, itaconic acid, lactic acid, gluconic acid, gluconate, lactic acid, succinic acid, 2,5-diketo-D-gluconic acid); ketones (e.g., acetone); amino acids (e.g., glutamic acid); gases (e.g., $H_2$ and $CO_2$), and more complex compounds, including, for example, antibiotics (e.g., penicillin and tetracycline); enzymes; vitamins (e.g., riboflavin, $B_{12}$, beta-carotene); and hormones. Fermentation is also commonly used in the consumable alcohol (e.g., beer and wine), dairy (e.g., in the production of yogurt and cheese), leather, and tobacco industries.

A vast number of processes of producing fermentation products, such as ethanol, by fermentation of sugars provided by degradation of starch-containing and/or lignocellulose-containing material are known in the art.

However, production of fermentation products, such as ethanol, from such plant materials is still too costly. Therefore, there is a need for providing processes that can increase the yield of the fermentation product and thereby reducing the production costs.

SUMMARY OF THE INVENTION

The present invention relates to processes of fermenting plant derived material into a fermentation product. The invention also provides processes of producing fermentation products from plant derived material using a fermenting organism. Finally the invention relates to compositions that are suitable for use in such processes of the invention.

According to the invention the starting material (i.e., substrate for the fermenting organism in question) may be any plant material or plant derived material. The material may be treated or untreated. The stating material may be starch-containing material. The starch material may be lignocellulose-containing material.

In the first aspect the invention relates to processes of fermenting plant material in a fermentation medium into a fermentation product using a fermenting organism, wherein one or more pyrophosphatase enzymes are present in the fermentation medium. According to the invention the concentration/dose level of pyrophosphatase(s) is(are) increased compared to when no pyrophosphatase is added before and/or during fermentation.

In the second aspect the invention relates to processes of producing a fermentation product from starch-containing material comprising the steps of:
i) liquefying starch-containing material;
ii) saccharifying the liquefied material; and
iii) fermenting with one or more fermenting organisms in accordance with the fermentation process of the invention.

In the third aspect the invention relates to processes of producing a fermentation product from starch-containing material, comprising the steps of:
(a) saccharifying starch-containing material at a temperature below the initial gelatinization temperature of said starch-containing material; and
(b) fermenting using a fermenting organism;
wherein fermentation is carried out in accordance with a fermentation process of the invention.

In the fourth aspect the invention relates to processes of producing a fermentation product from lignocellulose-containing material, comprising the steps of:
(a) pre-treating lignocellulose-containing material;
(b) hydrolyzing the material;
(c) fermenting using a fermenting organism in accordance with a fermentation process of the invention.

In the fifth aspect the invention relates to a composition comprising one or more pyrophosphatase enzymes.

In the sixth aspect the invention relates to the use of pyrophosphatase enzyme for improving the fermentation product yield and/or fermentation rate during a fermentation process.

In the seventh aspect the invention relates to a transgenic plant material transformed with a polynucleotide sequence encoding a pyrophosphatase enzyme.

In the eighths aspect the invention relates to modified fermenting organisms transformed with a polynucleotide encoding a pyrophosphatase enzyme, wherein the fermenting organism is capable of expressing pyrophosphatase enzyme at fermentation conditions.

DETAILED DESCRIPTION OF THE INVENTION

Figure 1A:
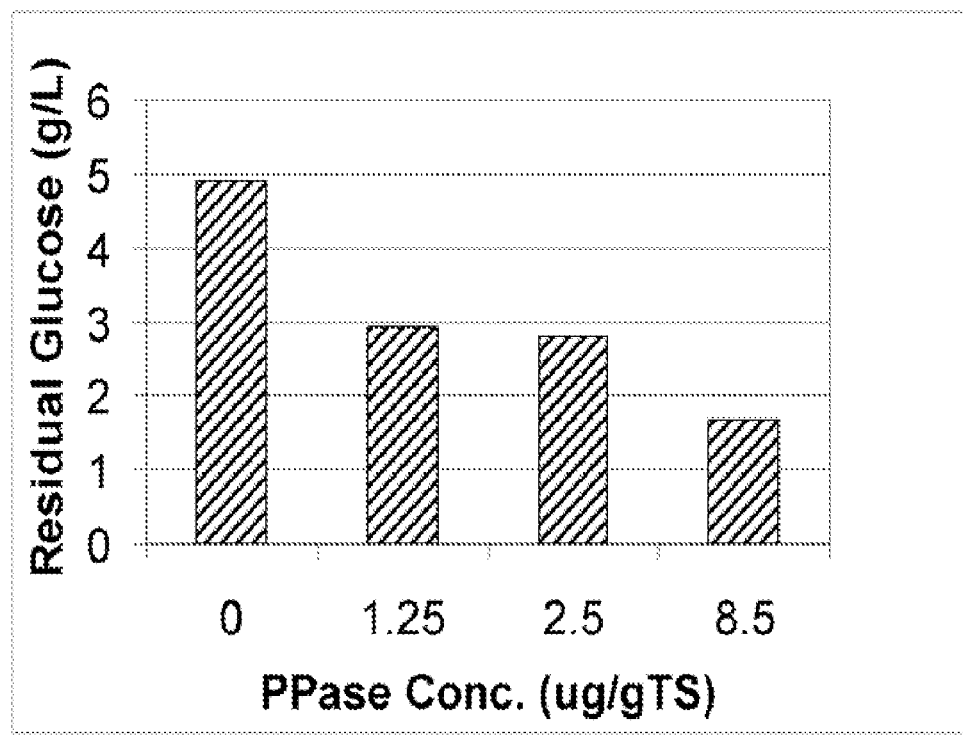
FIG. 1a. Effect of pyrophosphatase on residual glucose after 48 hour fermentation of PCS hydrolysates.

The present invention relates to processes of fermenting plant material into a desired fermentation product. The invention also provides processes of producing desired fermentation products from plant material using a fermenting organism. Finally the invention relates to a composition comprising one or more pyrophosphatases.

Yeast (*Saccharomyces cerevisiae*) experiences inhibition of cell growth, loss of cell viability, loss of nutrient uptake, decreased proton fluxes across the cytoplasmic membrane, and impaired fermentation performance when the ethanol concentration increases during ethanol fermentation. Ethanol first accumulates in the intracellular environment and is later released into the fermentation medium. As a result, the ethanol concentration experienced by cytosolic enzymes can be higher than the concentration in the fermentation medium and therefore potentially stressful to the yeast cells. Previous studies showed that cytosol pyrophosphatase is inhibited by ethanol during yeast fermentation which consequently impacts the yeast growth and its metabolic machinery (Lopes, D. H. J. "Urea increases tolerance of yeast inorganic pyrophosphatase activity to ethanol: The other side of urea interaction with proteins" (2001) Arch. Biochem. Biophys. (394) 61-66; Peres-Castineira, J. R. "Functional complementation of yeast cytosolic pyrophosphatase by bacterial and plant H+-translocating pyrophosphatases (2002) PNAS (99) 15914-15919).

The inventors have found that increased levels of pyrophosphatase, compared to when no pyrophosphatase is added to the fermentation medium, results in increased fermentation performance and subsequently increased fermentation yield.

It is believed that increased levels of pyrophosphatase in the fermentation medium maintain the yeast viability; sustain metabolic functionality; and results in less ethanol inflicted stress. Other factors including reduced loss of nutrient uptake may be accomplished too.

Consequently, in the first aspect the invention relates to processes of fermenting plant material in a fermentation medium into a fermentation product using a fermenting organism, wherein one or more pyrophosphatase enzymes are present in the fermentation medium. The pyrophosphatase enzyme(s) may be added/introduced before and/or during fermentation and/or may be produced in situ by, e.g., overexpression by the fermenting organisms, preferably yeast. The pyrophosphatase may also be introduced into the fermentation medium in the form of transgenic plant material containing or expressing pyrophosphatase.

Fermentation Medium

The phrase "fermentation media" or "fermentation medium" refers to the environment in which fermentation is carried out and comprises the fermentation substrate, that is, the carbohydrate source that is metabolized by the fermenting organism(s), and may include the fermenting organism(s).

The fermentation medium may comprise nutrients and growth stimulator(s) for the fermenting organism(s). Nutrient and growth stimulators are widely used in the art of fermentation and include nitrogen sources, such as ammonia; vitamins and minerals, or combinations thereof.

Following fermentation, the fermentation media or fermentation medium may further comprise the fermentation product.

Fermenting Organism

The phrase "fermenting organism" refers to any organism, including bacterial and fungal organisms, suitable for producing a desired fermentation product. The fermenting organism may be C6 or C5 fermenting organisms, or a combination thereof. Both C6 and C5 fermenting organisms are well known in the art.

Suitable fermenting organisms are able to ferment, i.e., convert, fermentable sugars, such as glucose, fructose, maltose, xylose, mannose and or arabinose, directly or indirectly into the desired fermentation product.

Examples of fermenting organisms include fungal organisms such as yeast. Preferred yeast includes strains of the genus *Saccharomyces*, in particular strains of *Saccharomyces cerevisiae* or *Saccharomyces uvarum*; a strain of *Pichia*, preferably *Pichia stipitis* such as *Pichia stipitis* CBS 5773 or *Pichia pastoris*: a strain of the genus *Candida*, in particular a strain of *Candida utilis*, *Candida arabinofermentans*, *Candida diddensil*, *Candida sonorensis*, *Candida shehatae*, *Candida tropicalis*, or *Candida boidinii*. Other fermenting organisms include strains of *Hansenula*, in particular *Hansenula polymorpha* or *Hansenula anamala*; *Kluyveromyces*, in particular *Kluyveromyces fragilis* or *Kluyveromyces marxianus*; and *Schizosaccharomyces*, in particular *Schizosaccharomyces pombe*.

Preferred bacterial fermenting organisms include strains of *Escherichia*, in particular *Escherichia coli*, strains of *Zymomonas*, in particular *Zymomonas mobilis*, strains of *Zymobacter*, in particular *Zymobactor palmae*, strains of *Klebsiella* in particular *Klebsiella oxytoca*, strains of *Leuconostoc*, in particular *Leuconostoc mesenteroides*, strains of *Clostridium*, in particular *Clostridium butyricum*, strains of *Enterobacter*, in particular *Enterobacter aerogenes* and strains of *Thermoanaerobacter*, in particular *Thermoanaerobacter* BG1L1 (Appl. Microbial. Biotech. 77: 61-86) and *Thermoanarobader ethanolicus*, *Thermoanaerobacter thermosaccharolyticum*, or *Thermoanaerobacter mathranii*. Strains of *Lactobacillus* are also envisioned as are strains of *Corynebacterium glutamicum R*, *Bacillus thermoglucosidaisus*, and *Geobacillus thermoglucosidasius*.

In an embodiment the fermenting organism is a C6 sugar fermenting organism, such as a strain of, e.g., *Saccharomyces cerevisiae*.

In connection with fermentation of lignocellulose derived materials, C5 sugar fermenting organisms are contemplated. Most C5 sugar fermenting organisms also ferment C6 sugars. Examples of C5 sugar fermenting organisms include strains of *Pichia*, such as of the species *Pichia stipitis*. C5 sugar fermenting bacteria are also known. Also some *Saccharomyces cerevisae* strains ferment C5 (and C6) sugars. Examples are genetically modified strains of *Saccharomyces* spp. that are capable of fermenting C5 sugars include the ones concerned in, e.g., Ho et al., 1998, *Applied and Environmental Microbiology*, p, 1852-1859 and Karhumaa et al., 2006, *Microbial Cell Factories* 5:18, and Kuyper et al., 2005, *FEMS Yeast Research* 5: 925-934.

In one embodiment the fermenting organism is added to the fermentation medium so that the viable fermenting organism, such as yeast, count per mL of fermentation medium is in the range from $10^5$ to $10^{12}$, preferably from $10^7$ to $10^{10}$, especially about $5 \times 10^7$.

Commercially available yeast includes, e.g., RED START™ and ETHANOL RED™ yeast (available from Fermentis/Lesaffre, USA), FALI (available from Fleischmann's Yeast, USA), SUPERSTART and THERMOSACC™ fresh yeast (available from Ethanol Technology, Wis., USA), BIOFERM AFT and XR (available from NABC—North American Bioproducts Corporation, Ga., USA), GERT STRAND (available from Gert Strand AB, Sweden), and FERMIOL (available from DSM Specialties).

According to the invention the fermenting organism capable of producing a desired fermentation product from fermentable sugars, such as, e.g., glucose, fructose maltose, xylose and/or arabinose, is preferably grown under precise conditions at a particular growth rate. When the fermenting organism is introduced into/added to the fermentation medium the inoculated fermenting organism pass through a number of stages. Initially growth does not occur. This period is referred to as the "lag phase" and may be considered a period of adaptation. During the next phase referred to as the "exponential phase" the growth rate gradually increases. After a period of maximum growth the rate ceases and the fermenting organism enters "stationary phase". After a further period of time the fermenting organism enters the "death phase" where the number of viable cells declines.

In one embodiment the pyrophosphatase(s) is(are) added to the fermentation medium when the fermenting organism is in lag phase.

In one embodiment the pyrophosphatase(s) added to the fermentation medium when the fermenting organism is in exponential phase.

In one embodiment the pyrophosphatase(s) is(are) added to the fermentation medium when the fermenting organism is in stationary phase.

Metal Ions

In an embodiment of the invention one or more metal ions, or alternatively compounds capable of releasing metal ions, may be added before and/or during fermentation. The metal ions may be added simultaneously with or separately from adding the pyrophosphatase enzyme(s). Metal ions, such as $Mg^{2+}$, $Mn^{2++}$ and $Zn^{2+}$, may have a boosting effect on the pyrophosphatase enzyme(s) activity. One skilled in the art can easily determine suitable amounts to add. In an embodiment metal ions, such as $Mg^{2+}$, are added in an amount in the range from above zero to 10 mM. In a preferred embodiment the metal ions are $Mn^{2+}$.

Fermentation Products

The term "fermentation product" means a product produced by a process including a fermentation step using a fermenting organism. Fermentation products contemplated according to the invention include alcohols (e.g., ethanol, methanol, butanol); organic acids (e.g., citric acid, acetic acid, itaconic acid, lactic acid, succinic acid, gluconic acid); ketones (e.g., acetone); amino acids (e.g. glutamic acid); gases (e.g., $H_2$ and $CO_2$), antibiotics (e.g., penicillin and tetracycline); enzymes; vitamins (e.g., riboflavin, $B_{12}$, beta-carotene); and hormones. In a preferred embodiment the fermentation product is ethanol, e.g. fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, happoushu, high-alcohol beer, low-alcohol beer, low-calorie beer or light beer. Preferred fermentation processes used include alcohol fermentation processes. The fermentation product, such as ethanol, obtained according to the invention, may preferably be used as fuel. However, in the case of ethanol it may also be used as potable ethanol.

Fermentation

The fermentation may according to the invention be carried out at conventionally used conditions. Preferred fermentation processes are anaerobic processes.

For instance, for ethanol production the fermentation may in one embodiment go on for 6 to 120 hours, in particular 24 to 96 hours. In an embodiment the fermentation is carried out at a temperature between 25° C. and 40° C., preferably 28° C. and 35° C., such as between 30° C. and 34° C., and in particular around 32° C. In an embodiment the pH when initiating fermentation is in the range from pH 3 to 6 (for fermentations based on lignocellulose derived material or starch derived material), preferably around pH 4 to 5 (for fermentations based on starch derived material).

Contemplated is simultaneous hydrolysis/saccharification and fermentation, meaning that the hydrolyzing/saccharifying enzyme(s), the fermenting organism and pyrophosphatase enzyme(s) may be added together. However, it should be understood that, e.g., the pyrophosphatase enzyme(s) may also be added separately. When fermentation is performed simultaneous with hydrolysis/saccharification the temperature is preferably between from 25° C. to 40° C., preferably from 28° C. to 35° C., such as from 30° C. to 34° C., in particular around 32° C., when the fermentation organism is a yeast, such as a strain of *Saccharomyces cerevisiae*, and the desired fermentation product is ethanol.

Other fermentation products may be fermented at conditions and temperatures, well known to the skilled person in the art, suitable for the fermenting organism in question.

The process of the invention may be performed as a batch or as a continuous process. The fermentation process of the invention may be conducted in an ultrafiltration system where the retentate is held under recirculation in the presence of solids, water, and the fermenting organism, and where the permeate is the desired fermentation product containing liquid. Equally contemplated if the process is conducted in a continuous membrane reactor with ultrafiltration membranes and where the retentate is held under recirculation in presence of solids, water, the fermenting organism and where the permeate is the fermentation product containing liquid.

After fermentation the fermenting organism may be separated from the fermented slurry and recycled to the fermentation medium.

Recovery

Subsequent to fermentation the fermentation product may be separated from the fermentation medium. The slurry may be distilled to extract the desired fermentation product or the desired fermentation product may be extracted from the fermentation medium by micro or membrane filtration techniques. Alternatively the fermentation product may be recovered by stripping. Methods for recovery are well known in the art.

Production of Fermentation Products from Starch-Containing Material

Processes for Producing Fermentation Products from Gelatinized Starch-Containing Material In this aspect the present invention relates to a process for producing a fermentation product, especially ethanol, from starch-containing material, which process includes a liquefaction step and sequentially or simultaneously performed saccharification and fermentation steps.

The invention relates to a process for producing a fermentation product from starch-containing material comprising the steps of
  i) liquefying starch-containing material:
  ii) saccharifying the liquefied material,
  iii) fermenting using one or more fermenting organisms,
wherein fermentation is carried out in accordance with a fermentation process of the invention, i.e., in the presence of pyrophosphatase enzyme(s).

Saccharification step ii) and fermentation step iii) may be carried out either sequentially or simultaneously. The pyrophosphatase enzyme(s) may be added before (e.g., during liquefaction step i) or separate saccharification step ii)) and/or during the fermentation step iii) or simultaneous saccharification and fermentation step.

The fermentation product, such as especially ethanol, may optionally be recovered after fermentation, e.g., by distillation. Suitable starch-containing starting materials are listed in the section "Starch-Containing Materials" section below. Contemplated enzymes are listed in the "Enzymes" section below. The liquefaction is preferably carried out in the presence of an alpha-amylase, preferably a bacterial alpha-amylase or acid fungal alpha-amylase. The fermentation organism is preferably yeast, preferably a strain of *Saccharomyces cer-*

*evisiae.* Suitable fermenting organisms are listed in the "Fermenting Organisms" section above.

In a particular embodiment, the process of the invention further comprises, prior to the step (i), the steps of:

x) reducing the particle size of the starch-containing material, preferably by milling:

y) forming a slurry comprising the starch-containing material and water.

The aqueous slurry may contain from 10-55 wt. % dry solids (DS), preferably 25-45 wt. % dry solids (DS), more preferably 30-40% dry solids (DS) of starch-containing material. The slurry is heated to above the gelatinization temperature and alpha-amylase, preferably bacterial and/or acid fungal alpha-amylase may be added to initiate liquefaction (thinning). The slurry may in an embodiment be jet-cooked to further gelatinize the slurry before being subjected to an alpha-amylase in step (i) of the invention.

Liquefaction may be carried out as a three-step hot slurry process. The slurry is heated to between 60-95° C., preferably 80-85° C., and alpha-amylase is added to initiate liquefaction (thinning). Then the slurry may be jet-cooked at a temperature between 95-140° C., preferably 105-125° C., for about 1-15 minutes, preferably for about 3-10 minutes, especially around about 5 minutes. The slurry is cooled to 60-95° C. and more alpha-amylase is added to finalize hydrolysis (secondary liquefaction). The liquefaction process is usually carried out at pH 4.5-6.5, in particular at a pH from 5 to 6.

The saccharification step (ii) may be carried out using conditions well know in the art. For instance, a full saccharification process may last up to from about 24 to about 72 hours, however, it is common only to do a pre-saccharification of typically 40-90 minutes at a temperature between 30-65° C., typically about 60° C., followed by complete saccharification during fermentation in a simultaneous saccharification and fermentation process (SSF process). Saccharification is typically carried out at temperatures from 20-75° C., preferably from 40-70° C., typically around 60° C., and at a pH between 4 and 5, normally at about pH 4.5.

The most widely used process in fermentation product, especially ethanol, production is the simultaneous saccharification and fermentation (SSF) process, in which there is no holding stage for the saccharification, meaning that fermenting organism, such as yeast, and enzyme(s), including pyrophosphatase enzyme(s), may be added together. SSF may typically be carried out at a temperature from 25° C. to 40° C., such as from 28° C. to 35° C., such as from 30° C. to 34° C., preferably around 32° C. According to the invention the temperature may be adjusted up or down during fermentation.

In accordance with the present invention the fermentation step (iii) includes, without limitation, fermentation processes of the invention used to produce fermentation products as exemplified above in the "Fermentation Products" section.

Processes for Producing Fermentation Products from Un-Gelatinized Starch-Containing Material In this aspect the invention relates to processes for producing a fermentation product from starch-containing material without gelatinization (often referred to as "without cooking") of the starch-containing material. According to the invention the desired fermentation product, such as ethanol, can be produced without liquefying the aqueous slurry containing the starch-containing material. In one embodiment a process of the invention includes saccharifying milled) starch-containing material, e.g. granular starch, below the initial gelatinization temperature, preferably in the presence of alpha-amylase and/or carbohydrate-source generating enzyme(s) to produce sugars that can be fermented into the desired fermentation product by a suitable fermenting organism.

In this embodiment the desired fermentation product, preferably ethanol, is produced from un-gelatinized (i.e., uncooked), preferably milled, cereal grains, such as corn.

Accordingly, in this aspect the invention relates to a process of producing a fermentation product from starch-containing material, comprising the steps of:

(a) saccharifying starch-containing material at a temperature below the initial gelatinization temperature of said starch-containing material;

(b) fermenting using a fermenting organism:

wherein the fermentation is carried out in accordance with a fermentation process of the invention, i.e., in the presence of pyrophosphatase enzyme(s).

In a preferred embodiment steps (a) and (b) are carried out simultaneously (i.e., one-step fermentation) or sequentially.

The fermentation product, such as especially ethanol, may optionally be recovered after fermentation, e.g., by distillation. Suitable starch-containing starting materials are listed in the section "Starch-Containing Materials" section below. Contemplated enzymes are listed in the "Enzymes." section below. Typically amylase(s), such as glucoamylase(s) and/or other carbohydrate-source generating enzymes and/or alpha-amylase(s), is(are) present during fermentation.

Examples of glucoamylases and other carbohydrate-source generating enzymes can be found below and includes raw starch hydrolyzing glucoamylases.

Examples of alpha-amylase(s) include acid alpha-amylases, preferably acid fungal alpha-amylases.

Examples of fermenting organisms include yeast, preferably a strain of *Saccharomyces cerevisiae*. Other suitable fermenting organisms are listed in the "Fermenting Organisms" section above.

The term "initial gelatinization temperature" means the lowest temperature at which starch gelatinization commences. In general, starch heated in water begins to gelatinize between about 50° C. and 75° C.; the exact temperature of gelatinization depends on the specific starch and can readily be determined by the skilled artisan. Thus, the initial gelatinization temperature may vary according to the plant species, to the particular variety of the plant species as well as with the growth conditions. In context of this invention the initial gelatinization temperature of a given starch-containing material may be determined as the temperature at which birefringence is lost in 5% of the starch granules using the method described by Gorinstein and Lii, 1992, Starch/Stärke, Vol. 44 (12): 461-466.

Before step (a) a slurry of starch-containing material, such as granular starch, having 10-55 wt. % dry solids (DS), preferably 25-45 wt. % dry solids, more preferably 30-40% dry solids of starch-containing material may be prepared. The slurry may include water and/or process waters, such as stillage (backset), scrubber water, evaporator condensate or distillate, side-stripper water from distillation, or process water from other fermentation product plants. Because the process of the invention is carried out below the initial gelatinization temperature and thus no significant viscosity increase takes place, high levels of stillage may be used if desired. In an embodiment the aqueous slurry contains from about 1 to about 70 vol. %, preferably 15-60% vol. %, especially from about 30 to 50 vol. % water and/or process waters, such as stillage (backset), scrubber water, evaporator condensate or distillate, side-stripper water from distillation, or process water from other fermentation product plants, or combinations thereof, or the like.

The starch-containing material may be prepared by reducing the particle size, preferably by dry or wet milling, to 0.05 to 3.0 mm, preferably 0.1-0.5 mm. After being subjected to a process of the invention at least 85%, at least 86%, at least 87%, at least 88%, at least 89%, at least 90%, at least 91%, at least 92%, at least 93%, at least 94%, at least 95%, at least 96%, at least 97%, at least 98%, or preferably at least 99% of the dry solids in the starch-containing material are converted into a soluble starch hydrolysate.

A process of the invention is conducted at a temperature below the initial gelatinization temperature, which means that the temperature at which step (a) is carried out typically lies in the range between 30-75° C., preferably between 45-60° C.

In a preferred embodiment steps (a) and (b) are carried out as a simultaneous saccharification and fermentation process. In such preferred embodiment the process is typically carried at a temperature from 25° C. to 40° C., such as from 28° C. to 35° C., such as from 30° C. to 34° C., preferably around 32° C.

In an embodiment fermentation is carried out so that the sugar level, such as glucose level, is kept at a low level, such as below 6 wt. %, such as below about 3 wt. %, such as below about 2 wt. %, such as below about 1 wt. %, such as below about 0.5 wt. %, or below 0.25 wt. %, such as below about 0.1 wt. %. Such low levels of sugar can be accomplished by simply employing adjusted quantities of enzyme and fermenting organism. A skilled person in the art can easily determine which doses/quantities of enzyme and fermenting organism to use. The employed quantities of enzyme and fermenting organism may also be selected to maintain low concentrations of maltose in the fermentation broth. For instance, the maltose level may be kept below about 0.5 wt. %, such as below about 0.2 wt. %.

The process of the invention may be carried out at a pH from about 3 and 7, preferably from pH 3.5 to 6, or more preferably from pH 4 to 5, Starch-Containing Materials Any suitable starch-containing starting material, including granular starch (raw uncooked starch), may be used according to the present invention. The starting material is generally selected based on the desired fermentation product. Examples of starch-containing starting materials, suitable for use in a process of present invention, include tubers, roots, stems, whole grains, corns, cobs, wheat, barley, rye, mile, sago, cassaya, tapioca, sorghum, rice peas, beans, or sweet potatoes, or mixtures thereof, or cereals. Contemplated are also waxy and non-waxy types of corn and barley.

The term "granular starch" means raw uncooked starch, i.e., starch in its natural form found in cereal, tubers or grains. Starch is formed within plant cells as tiny granules insoluble in water. When put in cold water, the starch granules may absorb a small amount of the liquid and swell. At temperatures up to 50° C. to 75° C. the swelling may be reversible. However, with higher temperatures an irreversible swelling called "gelatinization" begins. Granular starch to be processed may be a highly refined starch quality, preferably at least 90%, at least 95%, at least 97% or at least 99.5% pure or it may be a more crude starch-containing materials comprising (e.g., milled) whole grains including non-starch fractions such as germ residues and fibers. The raw material, such as whole grains, may be reduced in particle size, e.g., by milling, in order to open up the structure and allowing for further processing. Two processes are preferred according to the invention: wet and dry milling. In dry milling whole kernels are milled and used. Wet milling gives a good separation of germ and meal (starch granules and protein) and is often applied at locations where the starch hydrolysate is used in production of, e.g., syrups. Both dry and wet milling is well known in the art of starch processing and is equally contemplated for a process of the invention. In an embodiment the particle size is reduced to between 0.05 to 3.0 mm, preferably 0.1-0.5 mm, or so that at least 30%, preferably at least 50%, more preferably at least 70%, even more preferably at least 90% of the starch-containing material fit through a sieve with a 0.05 to 3.0 mm screen, preferably 0.1-0.5 mm screen.

Production of Fermentation Products from Lignocellulose-Containing Material

In this aspect, the invention relates to processes of producing fermentation products from lignocellulose-containing material. Conversion of lignocellulose-containing material into fermentation products, such as ethanol, has the advantages of the ready availability of large amounts of feedstock, including wood, agricultural residues, herbaceous crops, municipal solid wastes, etc. Lignocellulose-containing materials typically primarily consist of cellulose, hemicellulose, and lignin and are often referred to as "biomass".

The structure of lignocellulose is not directly accessible to enzymatic hydrolysis. Therefore, the lignocellulose-containing material has to be pre-treated, e.g., by acid hydrolysis under adequate conditions of pressure and temperature, in order to break the lignin seal and disrupt the crystalline structure of cellulose. This causes solubilization of the hemicellulose and cellulose fractions. The cellulose and hemicelluloses can then be hydrolyzed enzymatically, e.g., by cellulolytic enzymes, to convert the carbohydrate polymers into fermentable sugars which may be fermented into desired fermentation products, such as ethanol. Optionally the fermentation product may be recovered, e.g., by distillation.

In this aspect the invention relates to processes of producing a fermentation product from lignocellulose-containing material, comprising the steps of:

(a) pre-treating lignocellulose-containing material;
(b) hydrolyzing the material:
(c) fermenting with a fermenting organism in accordance with a fermentation process of the invention, i.e., in the presence of pyrophosphatase(s).

The pyrophosphatase(s) may be added before and/or during fermentation. Hydrolysis step (b) and fermentation step (c) may be carried out sequentially or simultaneously. In preferred embodiments the steps are carried out as SSF, HHF, or SHF process steps which will be described further below.

Pre-Treatment

The lignocellulose-containing material may according to the invention be pre-treated before being hydrolyzed and fermented, in a preferred embodiment the pre-treated material is hydrolyzed, preferably enzymatically, before and/or during fermentation. The goal of pre-treatment is to separate and/or release cellulose, hemicellulose and/or lignin and this way improve the rate of enzymatic hydrolysis.

According to the invention pre-treatment step (a) may be a conventional pre-treatment step known in the art. Pre-treatment may take place in aqueous slurry. The lignocellulose-containing material may during pre-treatment be present in an amount between 10-80 wt. %, preferably between 20-50 wt. %.

Chemical, Mechanical and/or Biological Pre-Treatment

The lignocellulose-containing material may according to the invention be chemically, mechanically and/or biologically pre-treated before hydrolysis and/or fermentation. Mechanical treatment (often referred to as physical pre-treatment) may be used alone or in combination with subsequent or simultaneous hydrolysis, especially enzymatic hydrolysis, to promote the separation and/or release of cellulose, hemicellulose and/or lignin.

Preferably, the chemical, mechanical and/or biological pre-treatment is carried out prior to the hydrolysis and/or fermentation. Alternatively, the chemical, mechanical and/or biological pre-treatment is carried out simultaneously with hydrolysis, such as simultaneously with addition of one or more cellulolytic enzymes, or other enzyme activities mentioned below, to release fermentable sugars, such as glucose and/or maltose.

In an embodiment of the invention the pre-treated lignocellulose-containing material is washed and/or detoxified before or after hydrolysis step (b). This may improve the fermentability of, e.g., dilute-acid hydrolyzed lignocellulose-containing material, such as corn stover. Detoxification may be carried out in any suitable way, e.g. by steam stripping, evaporation, ion exchange, resin or charcoal treatment of the liquid fraction or by washing the pre-treated material.

Chemical Pre-Treatment

According to the present invention "chemical pre-treatment" refers to any chemical treatment which promotes the separation and/or release of cellulose, hemicellulose and/or lignin. Examples of suitable chemical pre-treatment steps include treatment with; for example, dilute acid, lime, alkaline, organic solvent, ammonia, sulphur dioxide, carbon dioxide. Further, wet oxidation and pH-controlled hydrothermolysis are also contemplated chemical pre-treatments.

Preferably, the chemical pre-treatment is acid treatment, more preferably, a continuous dilute and/or mild acid treatment, such as, treatment with sulfuric acid, or another organic acid, such as acetic acid, citric acid, tartaric acid, succinic acid, or mixtures thereof. Other acids may also be used. Mild acid treatment means in the context of the present invention that the treatment pH lies in the range from 1-5, preferably from pH 1-3. In a specific embodiment the acid concentration is in the range from 0.1 to 2.0 wt. % acid, preferably sulphuric acid. The acid may be mixed or contacted with the material to be fermented according to the invention and the mixture may be held at a temperature in the range of 160-220° C., such as 165-195° C., for periods ranging from minutes to seconds, e.g. 1-60 minutes, such as 2-30 minutes or 3-12 minutes. Addition of strong acids, such as sulphuric acid, may be applied to remove hemicellulose. This enhances the digestibility of cellulose.

Cellulose solvent treatment, also contemplated according to the invention, has been shown to convert about 90% of cellulose to glucose. It has also been shown that enzymatic hydrolysis could be greatly enhanced when the lignocellulosic structure is disrupted. Alkaline $H_2O_2$, ozone, organosolv (uses Lewis acids, $FeCl_3$, $(Al)_2SO_4$ in aqueous alcohols), glycerol, dioxane, phenol, or ethylene glycol are among solvents known to disrupt cellulose structure and promote hydrolysis (Mosier et al., 2005, Bioresource Technology 96: 673-686).

Alkaline chemical pre-treatment with base, e.g., NaOH, $Na_2CO_3$ and/or ammonia or the like, is also within the scope of the invention. Pre-treatment methods using ammonia are described in, e.g., WO 2006/110891, WO 2006/110899, WO 2006/110900, WO 2006/110901, which are hereby incorporated by reference.

Wet oxidation techniques involve use of oxidizing agents, such as: sulphite based oxidizing agents or the like. Examples of solvent pre-treatments include treatment with DMSO (Dimethyl Sulfoxide) or the like. Chemical pre-treatment is generally carried out for 1 to 60 minutes, such as from 5 to 30 minutes, but may be carried out for shorter or longer periods of time dependent on the material to be pre-treated.

Other examples of suitable pre-treatment methods are described by Schell et al., 2003, Appl. Biochem and Biotechn. Vol. 105-108, p. 69-85, and Mosier et al., 2005, Bioresource Technology 96: 673-686, and US publication no. 2002/0164730, which references are hereby all incorporated by reference.

Mechanical Pre-Treatment

As used in context of the present invention the term "mechanical pre-treatment" refers to any mechanical or physical pre-treatment which promotes the separation and/or release of cellulose, hemicellulose and/or lignin from lignocellulose-containing material. For example, mechanical pre-treatment includes various types of milling, irradiation, steaming/steam explosion, and hydrothermolysis.

Mechanical pre-treatment includes comminution (mechanical reduction of the particle size). Comminution includes dry milling, wet milling and vibratory ball milling. Mechanical pre-treatment may involve high pressure and/or high temperature (steam explosion). In an embodiment of the invention high pressure means pressure in the range from 300 to 600 psi, preferably 400 to 500 psi, such as around 450 psi. In an embodiment of the invention high temperature means temperatures in the range from about 100 to 300° C., preferably from about 140 to 235° C. In a preferred embodiment mechanical pre-treatment is a batch-process, steam gun hydrolyzer system which uses high pressure and high temperature as defined above. A Sunds Hydrolyzer (available from Sunds Defibrator AB (Sweden) may be used for this.

Combined Chemical and Mechanical Pre-Treatment

In an embodiment of the invention both chemical and mechanical pre-treatments are carried out involving, for example, both dilute or mild acid pretreatment and high temperature and pressure treatment. The chemical and mechanical pretreatment may be carried out sequentially or simultaneously, as desired.

Accordingly, in a preferred embodiment, the lignocellulose-containing material is subjected to both chemical and mechanical pre-treatment to promote the separation and/or release of cellulose, hemicellulose and/or lignin.

In a preferred embodiment pre-treatment is carried out as a dilute or mild acid pre-treatment step. In another preferred embodiment pre-treatment is carried out as an ammonia fiber explosion step (or AFEX pre-treatment step), Biological Pre-Treatment As used in the present invention the term "biological pre-treatment" refers to any biological pre-treatment which promotes the separation and/or release of cellulose, hemicellulose, and/or lignin from the lignocellulose-containing material Biological pre-treatment techniques can involve applying lignin-solubilizing microorganisms (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh, P., and Singh. A., 1993. Physicochemical and biological treatments for enzymatic/microbial conversion of lignocellulosic biomass, *Adv. Appl. Microbial.* 39: 295-333; McMillan, J. D., 1994, Pretreating lignocellulosic biomass: a review, in *Enzymatic Conversion of Biomass for Fuels Production*, Himmel, M. E. Baker, J. O., and Overend, R. P., eds., ACS Symposium Series 566, American Chemical Society, Washington, D.C., chapter 15; Gong, C. S. Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241, Olsson, L., and Hahn-Hagerdal, B., 1996, Fermentation of lignocellulosic hydrolysates for ethanol production, *Enz. Microb. Tech.* 18: 312-331; and Vallander, L., and Eriksson, K.-E, L., 1990, Production of ethanol from lignocellulosic materials: State of the art, *Adv. Biochem. Eng./Biotechnol,* 42: 63-95).

Hydrolysis

Before and/or during fermentation the pre-treated lignocellulose-containing material may be hydrolyzed in order to break the lignin seal and disrupt the crystalline structure of cellulose. In a preferred embodiment hydrolysis is carried out enzymatically. According to the invention the pre-treated lignocellulose-containing material to be fermented may be hydrolyzed by one or more hydrolases (class E.C. 3 according to Enzyme Nomenclature), preferably one or more carbohydrases including cellulolytic enzymes and hemicellulolytic enzymes, or combinations thereof. Further, protease, alpha-amylase, glucoamylase and/or the like may also be present during hydrolysis and/or fermentation as the lignocellulose-containing material may include some, e.g., starchy and/or proteinaceous material.

The enzyme(s) used for hydrolysis may be capable of directly or indirectly converting carbohydrate polymers into fermentable sugars, such as glucose and/or maltose, which can be fermented into a desired fermentation product, such as ethanol.

In a preferred embodiment the carbohydrase(s) has(have) cellulolytic and/or hemicellulolytic enzyme activity.

In a preferred embodiment hydrolysis is carried out using a cellulolytic enzyme preparation further comprising one or more polypeptides having cellulolytic enhancing activity. In a preferred embodiment the polypeptide(s) having cellulolytic enhancing activity is(are) of family GH61A origin. Examples of suitable and preferred cellulolytic enzyme preparations and polypeptides having cellulolytic enhancing activity are described in the "Cellulolytic Enzymes" section and "Cellulolytic Enhancing Polypeptides" sections below.

Suitable enzymes are described in the "Enzymes" section below.

Hemicellulose polymers can be broken down by hemicellullolytic enzymes and/or acid hydrolysis to release its five and six carbon sugar components. The six carbon sugars (hexoses), such as glucose, galactose, arabinose, and mannose, can readily be fermented to fermentation products such as ethanol, acetone, butanol, glycerol, citric acid, fumaric acid, etc. by suitable fermenting organisms including yeast.

Yeast is the preferred fermenting organism for ethanol fermentation. Preferred are strains of *Saccharomyces*, especially strains of the species *Saccharomyces cerevisiae*, preferably strains which are resistant towards high levels of ethanol, i.e., up to, e.g., about 10, 12, 15 or 20 vol. % or more ethanol.

Enzymatic hydrolysis is preferably carried out in a suitable aqueous environment under conditions which can readily be determined by one skilled in the art. In a preferred embodiment hydrolysis is carried out at suitable, preferably optimal, conditions for the enzyme(s) in question.

Suitable process time, temperature and pH conditions can readily be determined by one skilled in the art. Preferably, hydrolysis is carried out at a temperature between 25 and 70° C., preferably between 40 and 60° C., especially around 50° C. The step is preferably carried out at a pH in the range from 3-8, preferably pH 4-6. Hydrolysis is typically carried out for between 12 and 96 hours, preferable 16 to 72 hours, more preferably between 24 and 48 hours, Fermentation of Lignocellulose Derived Material Fermentation of lignocellulose derived material is carried out in accordance with a fermentation process of the invention as described above.

Lignocellulose-Containing Material (Biomass)

Any suitable lignocellulose-containing material is contemplated in context of the present invention. Lignocellulose-containing material may be any material containing lignocellulose. In a preferred embodiment the lignocellulose-containing material contains at least 50 wt. %, preferably at least 70 wt. %, more preferably at least 90 wt. % lignocellulose. It is to be understood that the lignocellulose-containing material may also comprise other constituents such as cellulosic material, such as cellulose, hemicellulose and may also comprise constituents such as sugars, such as fermentable sugars and/or un-fermentable sugars.

Lignocellulose-containing material is generally found, for example, in the stems, leaves, hulls, husks, and cobs of plants or leaves, branches, and wood of trees. Lignocellulosic material can also be, but is not limited to, herbaceous material, agricultural residues, forestry residues, municipal solid wastes, waste paper, and pulp and paper mill residues. It is understood herein that lignocellulose-containing material may be in the form of plant cell wall material containing lignin, cellulose, and hemi-cellulose in a mixed matrix.

In an embodiment the lignocellulose-containing material is corn fiber, rice straw, pine wood, wood chips, poplar, wheat straw, switchgrass, bagasse, paper and pulp processing waste.

Other more specific examples include corn stover, corn cobs, corn fiber, hardwood such as poplar and birch, softwood, cereal straw such as wheat straw, switch grass, Miscanthus, rice hulls, municipal solid waste (MSW), industrial organic waste, office paper, or mixtures thereof.

In a preferred embodiment the lignocellulose-containing material is corn stover or corn cobs. In another preferred embodiment, the lignocellulose-containing material is corn fiber. In another preferred embodiment, the lignocellulose-containing material is switch grass. In another preferred embodiment, the lignocellulose-containing material is bagasse.

SSF, HHF and SHF

In one embodiment of the present invention, hydrolysis and fermentation is carried out as a simultaneous hydrolysis and fermentation step (SSF). In general this means that combined/simultaneous hydrolysis and fermentation are carried out at conditions (e.g., temperature and/or pH) suitable, preferably optimal, for the fermenting organism(s) in question.

In another embodiment hydrolysis step and fermentation step are carried out as hybrid hydrolysis and fermentation (HHF). HHF typically begins with a separate partial hydrolysis step and ends with a simultaneous hydrolysis and fermentation step. The separate partial hydrolysis step is an enzymatic cellulose saccharification step typically carried out at conditions (e.g., at higher temperatures) suitable, preferably optimal, for the hydrolyzing enzyme(s) in question. The subsequent simultaneous hydrolysis and fermentation step is typically carried out at conditions suitable for the fermenting organism(s) (often at lower temperatures than the separate hydrolysis step).

In another embodiment the hydrolysis and fermentation steps may also be carried out as separate hydrolysis and fermentation, where the hydrolysis is taken to completion before initiation of fermentation. This is often referred to as "SHF".

Enzymes

Even if not specifically mentioned in context of a process of the invention, it is to be understood that the enzyme(s) is(are) used in an "effective amount".

Pyrophosphatase Enzymes

In context of the present invention "pyrophosphatase enzyme" (abbreviated "PPase") includes enzymes within the following EC (Enzyme Commission) classes: EC 3.1.3.1 and EC 3.1.3.9, EC 3.6.1.1; EC 3.6.1.8, EC 3.6.1.9, EC 3.6.1.40. EC classes are based on recommendations of the Nomenclature Committee of the International Union of Biochemistry and Molecular Biology (IUBMB). Description of EC classes can be found on the internet, e.g., on www.expasy.org/enzyme/.

In a preferred embodiment the pyrophosphatase enzyme is an inorganic pyrophosphatase (EC. 3.6.1.1) also referred to as diphosphate phosphohydrolase and pyrophosphate phosphohydrolase.

The inorganic pyrophosphatase catalyzes the following reaction:

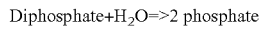

Diphosphate+H$_2$O=>2 phosphate

The specificity may vary with the source and with the activating metal ion and the enzyme from some sources may be identical with EC 3.1.3.1 or EC 3.1.3.9.

Inorganic PPases play an important role in energy metabolism, providing a thermodynamic pull for biosynthesis reactions such as protein, RNA and DNA synthesis (Lahti et al., "Cloning and characterization of the gene encoding inorganic pyrophosphatase of *E. coli* K-12", 1988, J. Bacteriol. 170: 5901-5907). According to Peller, "On the free-energy changes in the synthesis and degradation of nucleic acids, 1976, Biochemistry 15: 141-146, nucleic acid syntheses would be energetically impossible in viva if they were not coupled to the hydrolysis of pyrophosphate (PPi), catalyzed by pyrophosphatase. In addition, pyrophosphatase is important in the regulation of macromolecular synthesis and growth, and the glycolysis process of PPi-dependent phosphofructokinase reaction. Furthermore, the hydrolysis of PPi is coupled to the transport of hydrogen ions across a membrane, thus enhance proton pumping.

According to the invention any pyrophosphatase enzyme (PPase) may be present and/or added during a fermentation process of the invention.

The pyrophosphatase enzyme(s) is(are) according to the invention present and/or added in an effective amount so that the enzyme(s) provide(s) an improvement. e.g., higher fermentation yields, compared to a corresponding process carried out without having a pyrophosphatase enzyme present/added.

A vast number of pyrophosphatase enzymes are know in the art and may be found in, e.g., on the internet (see www.expasy.org/enzyme/).

In a preferred embodiment the pyrophosphatase enzyme is of microbial origin, such as bacterial or fungal, such as yeast or filamentous fungus origin. In another embodiment the pyrophosphatase enzyme is of mammalian or plant origin. In an embodiment the pyrophosphatase is acidic, which means that it has a pH optimum below pH 7.

Examples of pyrophosphatase enzymes include those derived from bacteria, such as a strain of the genus *Bacillus*, such as a strain of *Bacillus stearothermophilus*; or a strain of the genus *Thermoplasma*, such as a strain of *Thermoplasma acidophilum*; or a strain of the genus *Thermus*, such as a strain of *Thermus thermophilus*; or a strain of *Escherichia*, such as a strain of *Escherichia coli*; or from a filamentous fungus, such as strain of the genus *Aspergillus*, such as a strain of *Aspergillus niger*, or from yeast, such as a strain of the genus *Saccharomyces*, such as a strain of *Saccharomyces cerevisae*.

In another embodiment the pyrophosphatase is derived from the plant tobacco.

According to the invention the pyrophosphatase enzyme(s) is(are) added in effective amounts which means that the pyrophosphatase enzyme(s) is(are) present and/or added to the fermentation medium in concentrations in the range from 0.1 to 1,000 Units/g dry solids (DS), preferably from 1 to 100 Units/g dry solids (DS) when using the PPase Assay for yeast or in the range from 0.001 to 5 Units/g dry solids (DS), preferably from 0.01 to 1.5 Units/g dry solids (DS) when using the PPase Assay for bacteria. Both PPase Assays are described in the "Materials & Methods"-section below.

Commercially available pyrophosphatase products include those from *Saccharomyces cerevisae, Bacillus stearothermophilus, E. coli* and tobacco available from Sigma-Aldrich.

Alpha-Amylase

According to the invention any alpha-amylase may be used. Preferred alpha-amylases are of microbial, such as bacterial or fungal origin. Which alpha-amylase is the most suitable depends on the process conditions but can easily be determined by one skilled in the art.

In one embodiment the preferred alpha-amylase is an acid alpha-amylase, e.g., fungal acid alpha-amylase or bacterial acid alpha-amylase. The phrase "acid alpha-amylase" means an alpha-amylase (E.C. 3.2.1.1) which added in an effective amount has activity optimum at a pH in the range of 3 to 7, preferably from 3.5 to 6, or more preferably from 4-5.

Bacterial Alpha-Amylase

According to the invention a bacterial alpha-amylase is preferably derived from the genus *Bacillus*.

In a preferred embodiment the *Bacillus* alpha-amylase is derived from a strain of *Bacillus licheniformis, Bacillus amyloliquefaciens, Bacillus subtilis* or *Bacillus stearothermophilus*, but may also be derived from other *Bacillus* sp. Specific examples of contemplated alpha-amylases include the *Bacillus licheniformis* alpha-amylase shown in SEQ ID NO: 4 in WO 99/19467, the *Bacillus amyloliquefaciens* alpha-amylase SEQ ID NO: 5 in WO 99/19467 and the *Bacillus stearothermophilus* alpha-amylase shown in SEQ ID NO: 3 in WO 99/19467 (all sequences hereby incorporated by reference). In an embodiment the alpha-amylase may be an enzyme having a degree of identity of at least 60%, preferably at least 70%, more preferred at least 80%, even more preferred at least 90%, such as at least 95%, at least 96%, at least 97%, at least 98% or at least 99% to any of the sequences shown in SEQ ID NOS: 1, 2 or 3, respectively, in WO 99/19467.

The *Bacillus* alpha-amylase may also be a variant and/or hybrid, especially one described in any of WO 96/23873, WO 96/23874, WO 97/41213, WO 99/19467, WO 00/60059, and WO 02/10355 (all documents hereby incorporated by reference). Specifically contemplated alpha-amylase variants are disclosed in U.S. Pat. Nos. 6,093,562, 6,297,038 or 6,187,576 (hereby incorporated by reference) and include *Bacillus stearothermophilus* alpha-amylase (BSG alpha-amylase) variants having a deletion of one or two amino acid in positions R179 to G182, preferably a double deletion disclosed in WO 1996/023873—see e.g., page 20, lines 1-10 (hereby incorporated by reference), preferably corresponding to delta (181-182) compared to the wild-type BSG alpha-amylase amino acid sequence set forth in SEQ ID NO:3 disclosed in WO 99/19467 or deletion of amino acids R179 and G180 using SEQ ID NO:3 in WO 99/19467 for numbering (which reference is hereby incorporated by reference). Even more preferred are *Bacillus* alpha-amylases, especially *Bacillus stearothermophilus* alpha-amylase, which have a double deletion corresponding to delta(181-182) and further comprise a N193F substitution (also denoted I181*+G182*+N193F) compared to the wild-type BSG alpha-amylase amino acid sequence set forth in SEQ ID NO:3 disclosed in WO 99/19467.

Bacterial Hybrid Alpha-Amylase

A hybrid alpha-amylase specifically contemplated comprises 445 C-terminal amino acid residues of the *Bacillus*

*licheniformis* alpha-amylase (shown in SEQ ID NO: 4 of WO 99/19467) and the 37 N-terminal amino acid residues of the alpha-amylase derived from *Bacillus amyfoliquefaciens* (shown in SEQ ID NO: 5 of WO 99/19467), with one or more, especially all, of the following substitution:

G48A+T49I+G107A+H156Y+A181T+N190F+I201F+ A209V+Q264S (using the *Bacillus licheniformis* numbering in SEQ ID NO: 4 of WO 99/19467). Also preferred are variants having one or more of the following mutations (or corresponding mutations in other *Bacillus* alpha-amylase backbones): H154Y, A181T, N190F, A209V and Q264S and/or deletion of two residues between positions 176 and 179, preferably deletion of E178 and G179 (using the SEQ ID NO: 5 numbering of WO 99/19467).

In an embodiment the bacterial alpha-amylase is dosed in an amount of 0.0005-5 KNU per g DS, preferably 0.001-1 KNU per g DS, such as around 0.050 KNU per g DS.

Fungal Alpha-Amylase

Fungal alpha-amylases include alpha-amylases derived from a strain of the genus *Aspergillus*, such as, *Aspergillus oryzae, Aspergillus niger* and *Aspergillis kawachii* alpha-amylases.

A preferred acidic fungal alpha-amylase is a Fungamyl-like alpha-amylase which is derived from a strain of *Aspergillus oryzae*, According to the present invention, the term "Fungamyl-like alpha-amylase" indicates an alpha-amylase which exhibits a high identity, i.e., at least 70%, at least 75%, at least 80%, at least 85%, at least 90%, at least 95%, at least 96%, at least 97%, at least 98%, at least 99% or even 100% identity to the mature part of the amino acid sequence shown in SEQ ID NO: 10 in WO 96/23874.

Another preferred acid alpha-amylase is derived from a strain *Aspergillus niger*. In a preferred embodiment the acid fungal alpha-amylase is the one from *Aspergillus niger* disclosed as "AMYA_ASPNG" in the Swiss-prot/TeEMBL database under the primary accession no. P56271 and described in WO 89/01969 (Example 3—incorporated by reference). A commercially available acid fungal alpha-amylase derived from *Aspergillus niger* is SP288 (available from Novozymes A/S, Denmark).

Other contemplated wild-type alpha-amylases include those derived from a strain of the genera *Rhizomucor* and *Meripilus*, preferably a strain of *Rhizomucor pusillus* (WO 2004/055178 incorporated by reference) or *Meripilus giganteus*.

In a preferred embodiment the alpha-amylase is derived from *Aspergillus kawachii* and disclosed by Kaneko et al., 1996, J. Ferment. Bioeng. 81:292-298, "Molecular-cloning and determination of the nucleotide-sequence of a gene encoding an acid-stable alpha-amylase from *Aspergillus kawachii*"; and further as EMBL:#AB008370.

The fungal alpha-amylase may also be a wild-type enzyme comprising a starch-binding domain (SBD) and an alpha-amylase catalytic domain non-hybrid), or a variant thereof. In an embodiment the wild-type alpha-amylase is derived from a strain of *Aspergillus kawachii*.

Fungal Hybrid Alpha-Amylase

In a preferred embodiment the fungal acid alpha-amylase is a hybrid alpha-amylase. Preferred examples of fungal hybrid alpha-amylases include the ones disclosed in WO 2005/003311 or U.S. Patent Publication No. 2005/0054071 (Novozymes) or U.S. patentapplication No. 60/638,614 (Novozymes) which is hereby incorporated by reference. A hybrid alpha-amylase may comprise an alpha-amylase catalytic domain (CD) and a carbohydrate-binding domain/module (CBM), such as a starch binding domain, and optional a linker.

Specific examples of contemplated hybrid alpha-amylases include those disclosed in Table 1 to 5 of the examples in U.S. patent application No. 60/638,614, including Fungamyl variant with catalytic domain JA118 and *Atheha rolfsii* SBD (SEQ ID NO:100 in U.S. Pat. No. 60/638,614), *Rhizomucor pusillus* alpha-amylase with *Athelia rolfsii* AMG linker and SBD (SEQ ID NO:101 in U.S. Pat No. 60/638,614), *Rhizomucor pusillus* alpha-amylase with *Aspergillus niger* glucoamylase linker and SBD (which is disclosed in Table 5 as a combination of amino acid sequences SEQ ID NO:20, SEQ ID NO:72 and SEQ ID NO:96 in U.S. application Ser. No. 11/316,535) or as V039 in Table 5 in WO 2006/069290, and *Meripilus giganteus* alpha-amylase with *Athelia rolfsii* glucoamylase linker and SBD (SEQ ID NO:102 in U.S. 60/638, 614). Other specifically contemplated hybrid alpha-amylases are any of the ones listed in Tables 3, 4, 5, and 6 in Example 4 in U.S. application Ser. No. 11/316,535 and WO 2006/069290 (hereby incorporated by reference).

Other specific examples of contemplated hybrid alpha-amylases include those disclosed in U.S. Patent Publication No. 2005/0054071, including those disclosed in Table 3 on page 15, such as *Aspergillus niger* alpha-amylase with *Aspergillus kawachii* linker and starch binding domain.

Contemplated are also alpha-amylases which exhibit a high identity to any of above mention alpha-amylases, i.e., at least 70%, at least 75%, at least 80%, at least 85%, at least 90%, at least 95%, at least 96%, at least 97%, at least 98%, at least 99% or even 100% identity to the mature enzyme sequences.

An acid alpha-amylases may according to the invention be added in an amount of 0.001 to 10 AFAU/g DS, preferably from 0.01 to 5 AFAU/g DS, especially 0.3 to 2 AFAU/g DS or 0.001 to 1 FAU-F/g DS, preferably 0.01 to 1 FAU-F/g DS, Commercial Alpha-Amylase Products Preferred commercial compositions comprising alpha-amylase include MYCOLASET™ from DSM (Gist Brocades), BAN™, TERMAMYL™ SC, FUNGAMYL™, LIQUOZYME™ X, LIQUOZYME™ SC and SAN™ SUPER, SAN™ EXTRA L (Novozymes A/S) and CLARASE™ L-40,000, DEX-LO™, SPEZYME™ FRED, SPEZYME™ AA, and SPEZYME™ DELTA AA (Genencor Int.), and the acid fungal alpha-amylase sold under the trade name SP288 (available from Novozymes A/S, Denmark).

Carbohydrate-Source Generating Enzyme

The term "carbohydrate-source generating enzyme" includes glucoamylase (being glucose generators), beta-amylase and maltogenic amylase (being maltose generators) and also pullulanase and alpha-glucosidase. A carbohydrate-source generating enzyme is capable of producing a carbohydrate that can be used as an energy-source by the fermenting organism(s) in question, for instance, when used in a process of the invention for producing a fermentation product, such as ethanol. The generated carbohydrate may be converted directly or indirectly to the desired fermentation product, preferably ethanol. According to the invention a mixture of carbohydrate-source generating enzymes may be used. Especially contemplated mixtures are mixtures of at least a glucoamylase and an alpha-amylase, especially an acid amylase, even more preferred an acid fungal alpha-amylase. The ratio between acid fungal alpha-amylase activity (FAU-F) and glucoamylase activity (AGU) (i.e., FAU-F per AGU) may in an embodiment of the invention be between 0.1 and 100 AGU/FAU-F, in particular between 2 and 50 AGU/FAU-F, such as in the range from 10-40 AGU/FAU-F Glucoamylase A glucoamylase used according to the invention may be derived from any suitable source, e.g., derived from a micro-organism or a plant. Preferred glucoamylases are of fungal or bacterial origin, selected from the group consisting of *Aspergillus* glucoamylases, in particular *Aspergillus niger* G1 or G2 glucoamylase (Boel et al., 1984, EMBO J. 3(5): 1097-1102), or variants thereof, such as those disclosed in WO 92/00381, WO 00/04136 and WO 01/04273 (from Novozymes, Denmark); the *A. awamori* glucoamylase disclosed in WO 84/02921, *Aspergillus oryzae* glucoamylase (1991, Agric. Biol. Chem., 55(4): 941-949), or variants or fragments thereof. Other *Aspergillus* glucoamylase variants include variants with enhanced thermal stability; G137A and G139A (Chen et al. (1996), Prot. Eng, 9, 499-505); D257E and D293E/Q (Chen et al., 1995, Prot. Eng. 8: 575-582); N182 (Chen et al., 1994, Biochem. J. 301: 275-281); disulphide bonds, A246C (Fierobe et al., 1996. Biochemistry, 35: 8698-8704; and introduction of Pro residues in position A435 and S436 (Li at al., 1997, Protein Eng. 10; 1199-1204.

Other glucoamylases include *Athelia rolfsii* (previously denoted *Corticium rolfsii* glucoamylase (see U.S. Pat. No. 4,727,026 and Nagasaka. at al., 1998, "Purification and properties of the raw-starch-degrading glucoamylases from *Corticium rolfsii*, Appl Microbiol Biotechnol, 50:323-330), *Talaromyces* glucoamylases, in particular derived from *Talaromyces emersonii* (WO 99/28448), *Talaromyces leycettanus* (U.S. Pat. No. Re. 32,153), *Talaromyces duponti, Talaromyces thermophilus* (U.S. Pat. No. 4,587,215).

Bacterial glucoamylases contemplated include glucoamylases from the genus *Clostridium*, in particular *C. themioamylolyticum* (EP 135,138), and *C. thermohydrosulfuricum* (WO 86/01831) and *Trametes cingulata, Pachykytospora papyracea*; and *Leucopaxillus giganteus*, all disclosed in WO 2006/069289; or *Peniophora rufomarginata* disclosed in PCT/US2007/066618; or a mixture thereof. Also hybrid glucoamylase are contemplated according to the invention. Examples the hybrid glucoamylases disclosed in WO 2005/045018. Specific examples include the hybrid glucoamylase disclosed in Table 1 and 4 of Example 1 (which hybrids are hereby incorporated by reference).

Contemplated are also glucoamylases which exhibit a high identity to any of above mention glucoamylases, i.e., at least 70%, at least 75%, at least 80%, at least 85%, at least 90%, at least 95%, at least 96%, at least 97%, at least 98%, at least 99% or even 100% identity to the mature enzymes sequences mentioned above.

Commercially available compositions comprising glucoamylase include AMG 200L; AMG 300 L; SAN™ SUPER. SAN™ EXTRA L, SPRIZYME™ PLUS, SPIRIZYME™ FUEL, SPIRIZYME™ B4U and AMG™ E (from Novozymes A/S); OPTIDEX™ 300 (from Genencor Int.); AMIGASE™ and AMIGASE™ PLUS (from DSM); G-ZYME™ G900, G-ZYME™ and G990 ZR (from Genencor Int.).

Glucoamylases may in an embodiment be added in an amount of 0.0001-20 AGU/g DS, preferably 0.001-10 AGU/g DS, especially between 0.01-5 AGU/g DS, such as 0.1-2 AGU/g DS.

Beta-Amylase

A beta-amylase (E.C 3.2.1.2) is the name traditionally given to exo-acting maltogenic amylases, which catalyze the hydrolysis of 1,4-alpha-glucosidic linkages in amylose, amylopectin and related glucose polymers. Maltose units are successively removed from the non-reducing chain ends in a step-wise manner until the molecule is degraded or, in the case of amylopectin, until a branch point is reached. The maltose released has the beta anomeric configuration, hence the name beta-amylase.

Beta-amylases have been isolated from various plants and microorganisms W. M. Fogarty and C. T. Kelly, 1979, Progress in Industrial Microbiology, 15: 112-115). These beta-amylases are characterized by having optimum temperatures in the range from 40° C. to 65° C. and optimum pH in the range from 4.5 to 7. A commercially available beta-amylase from barley is NOVOZYM™ WBA from Novozymes A/S. Denmark and SPEZYME™ BBA 1500 from Genencor Int., USA.

Maltogenic Amylase

The amylase may also be a maltogenic alpha-amylase. A "maltogenic alpha-amylase" (glucan 1,4-alpha-maltohydrolase, E.C. 3.2.1.133) is able to hydrolyze amylose and amylopectin to maltose in the alpha-configuration. A maltogenic amylase from *Bacillus stearothermophilus* strain NCIB 11837 is commercially available from Novozymes A/S. Maltogenic alpha-amylases are described in U.S. Pat. Nos. 4,598, 048, 4,604,355 and 6,162,628, which are hereby incorporated by reference.

The maltogenic amylase may in a preferred embodiment be added in an amount of 0.05-5 mg total protein/gram DS or 0.05-5 MANU/g DS.

Cellulolytic Activity

The term "cellulolytic activity" as used herein are understood as comprising enzymes having cellobiohydrolase activity (EC 3.2.1.91), e.g., cellobiohydrolase I and cellobiohydrolase II, as well as endo-glucanase activity (EC 3.2.1.4) and beta-glucosidase activity (EC 3.2.1.21).

At least three categories of enzymes are important for converting cellulose into fermentable sugars: endo-glucanases (EC 3.2.1.4) that cut the cellulose chains at random; cellobiohydrolases (EC 3.2.1.91) which cleave cellobiosyl units from the cellulose chain ends and beta-glucosidases (EC 3.2.1.21) that convert cellobiose and soluble cellodextrins into glucose. Among these three categories of enzymes involved in the biodegradation of cellulose, cellobiohydrolases seems to be the key enzymes for degrading native crystalline cellulose.

The cellulolytic activity may, in a preferred embodiment, be in the form of a preparation of enzymes of fungal origin, such as from a strain of the genus *Trichoderma*, preferably a strain of *Trichoderma reesei*; a strain of the genus *Humicola*, such as a strain of *Humicola insolens*; or a strain of *Chrysosporium*, preferably a strain of *Chrysosporium lucknowense*.

In preferred embodiment the cellulolytic enzyme preparation contains one or more of the following activities: cellulase, hemicellulase, cellulolytic enzyme enhancing activity, beta-glucosidase activity, endoglucanase, cellubiohydrolase, or xylose-isomerase.

In a preferred embodiment cellulolytic enzyme preparation is a composition concerned in co-pending application PCT/US2008/065417, which is hereby incorporated by reference. In a preferred embodiment the cellulolytic enzyme preparation comprising a polypeptide having cellulolytic enhancing activity, preferably a family GH61A polypeptide, preferably the one disclosed in WO 2005/074656 (Novozymes). The cellulolytic enzyme preparation may further comprise a beta-glucosidase, such as a beta-glucosidase derived from a strain of the genus *Trichoderma, Aspergillus* or *Penicillium*, including the fusion protein having beta-glucosidase activity disclosed in co-pending application WO 2008/057637 (Novozymes). In a preferred embodiment the cellulolytic enzyme preparation may also comprises a CBH II enzyme, preferably *Thielavia terrestris* cellobiohydrolase II (CEL6A). In another preferred embodiment the cellulolytic enzyme preparation may also comprises cellulolytic enzymes, preferably one derived from *Trichoderma reesei* or *Humicola insolens*.

In a preferred embodiment the cellulolytic enzyme preparation may also comprising a polypeptide having cellulolytic enhancing activity (GH61A) disclosed in WO 2005/074656; a beta-glucosidase (fusion protein disclosed in WO 2008/057637) and cellulolytic enzymes derived from *Trichoderma reesei*.

In an embodiment the cellulolytic enzyme composition is the commercially available product CELLUCLAST™ 1.5L, CELLUZYME™ (from Novozymes A/S, Denmark) or ACCELERASE™ 1000 (from Genencor Inc. USA).

A cellulolytic enzyme may be added for hydrolyzing the pre-treated lignocellulose-containing material. The cellulolytic enzyme may be dosed in the range from 0.1-100 FPU per gram total solids (TS), preferably 0.5-50 FPU per gram TS, especially 1-20 FPU per gram TS. In another embodiment at least 0.1 mg cellulolytic enzyme per gram total solids (TS), preferably at least 3 mg cellulolytic enzyme per gram TS, such as between 5 and 10 mg cellulolytic enzyme(s) per gram TS is(are) used for hydrolysis.

Endoglucanase (EG)

The term "encloglucanase" means an endo-1,4-(1,3;1,4)-beta-D-glucan 4-glucanohydrolase (E.C. No. 3.2.1.4), which catalyzes endo-hydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity may be determined using carboxymethyl cellulose (CMC) hydrolysis according to the procedure of Ghose, 1987, *Pure and Appl. chem.* 59: 257-268.

In a preferred embodiment endoglucanases may be derived from a strain of the genus *Trichoderma*, preferably a strain of *Trichoderma reesei*; a strain of the genus *Humicola*, such as a strain of *Humicola insolens*; or a strain of *Chrysosporium*, preferably a strain of *Chrysosporium lucknowense*.

Cellobiohydrolase (CBH)

The term "cellobiohydrolase" means a 1,4-beta-D-glucan cellobiohydrolase (E.C. 3.2.1.91), which catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain.

Examples of cellobiohydroloses are mentioned above including CBH I and CBH II from *Trichoderma reseei: Humicola insolens* and CBH II from *Thielavia terrestris* cellobiohydrolase (CELL6A).

Cellobiohydrolase activity may be determined according to the procedures described by Lever et al., 1972, *Anal. Biochem.* 47: 273-279 and by van Tilbeurgh et al., 1982, *FEBS Letters* 149: 152-156; van Tilbeurgh and Claeyssens, 1985, *FEBS Letters* 187: 283-288. The Lever et al. method is suitable for assessing hydrolysis of cellulose in corn stover and the method of van Tilbeurgh et al. is suitable for determining the cellobiohydrolase activity on a fluorescent disaccharide derivative.

Beta-Glucosidase

One or more beta-glucosidases may be present during hydrolysis.

The term "beta-glucosidase" means a beta-D-glucoside glucohydrolase (E.C. 3.2.1.21), which catalyzes the hydrolysis of terminal non-reducing beta-D-glucose residues with the release of beta-D-glucose. For purposes of the present invention, beta-glucosidase activity is determined according to the basic procedure described by Venturi et al., 2002, *J. Basic Microbiol.* 42: 55-66, except different conditions were employed as described herein. One unit of beta-glucosidase activity is defined as 1.0 μmole of p-nitrophenol produced per minute at 50° C., pH 5 from 4 mM p-nitrophenyl-beta-D-glucopyranoside as substrate in 100 mM sodium citrate, 0.01% TWEEN® 20.

Figure 1B:
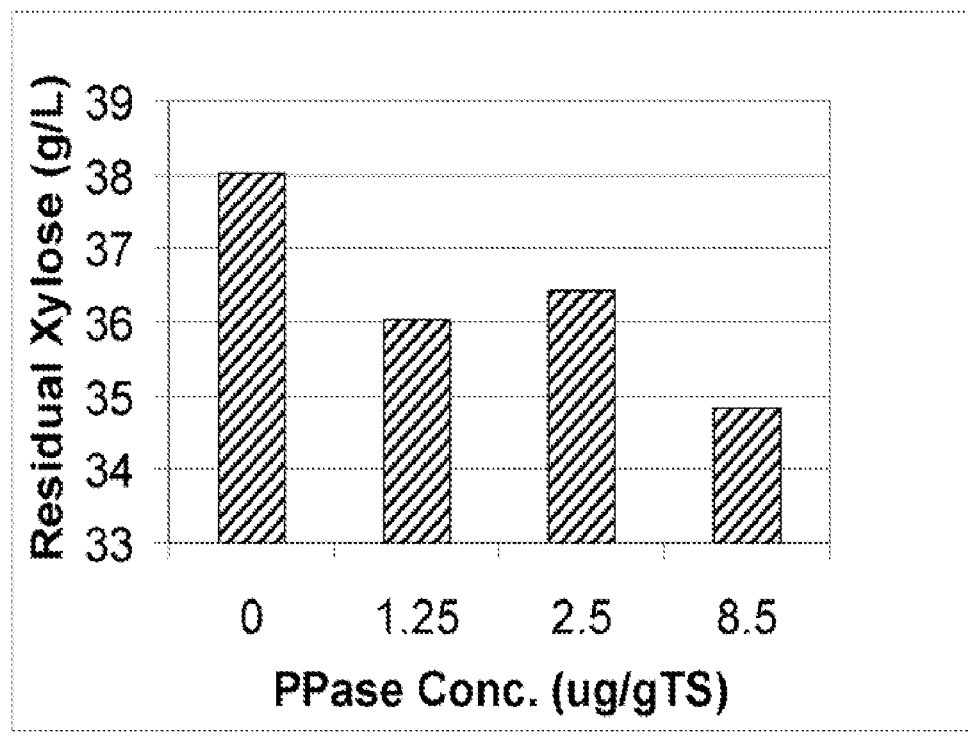
FIG. 1b. Effect of pyrophosphatase on residual xylose after 48 hour fermentation of PCS hydrolysates.

In a preferred embodiment the beta-glucosidase is of fungal origin, such as a strain of the genus *Trichoderma, Aspergillus* or *Penicillium*. In a preferred embodiment the beta-glucosidase is a derived from *Trichoderma reesei*, such as the beta-glucosidase encoded by the bgl1 gene (see FIG. 1 of EP 562003). In another preferred embodiment the beta-glucosidase is derived from *Aspergillus oryzae* (recombinantly produced in *Aspergillus oryzae* according to WO 02/095014), *Aspergillus fumigatus* (recombinanty produced in *Aspergillus oryzae* according to Example 22 of WO 02/095014) or *Aspergillus niger* (1981, J. Appl. 3: 157-163).

Hemicellulolytic Enzymes

According to the invention the pre-treated lignocellulose-containing material may further be subjected to one or more hemicellulolytic enzymes, e.g. one or more hemicellulases.

Hemicellulose can be broken down by hemicellulases and/or acid hydrolysis to release its five and six carbon sugar components.

In an embodiment of the invention the lignocellulose derived material may be treated with one or more hemicellulases.

Any hemicellulase suitable for use in hydrolyzing hemicellulose, preferably into xylose, may be used. Preferred hemicellulases include xylanases, arabinofuranosidases, acetyl xylan esterase, feruloyl esterase, glucuronidases, endo-galactanase, mannases, endo or exo arabinases, exo-galactanses, and mixtures of two or more thereof. Preferably, the hemicellulase for use in the present invention is an exo-acting hemicellulase, and more preferably, the hemicellulase is an exo-acting hemicellulase which has the ability to hydrolyze hemicellulose under acidic conditions of below pH 7, preferably pH 3-7. An example of hemicellulase suitable for use in the present invention includes VISCOZYME™ (available from Novozymes A/S, Denmark).

In an embodiment the hemicellulase is a xylanase. In an embodiment the xylanase may preferably be of microbial origin, such as of fungal origin (e.g., *Trichoderma, Meripilus, Humicola, Aspergillus, Fusarium*) or from a bacterium (e.g., *Bacillus*). In a preferred embodiment the xylanase is derived from a filamentous fungus, preferably derived from a strain of *Aspergillus*, such as *Aspergillus aculeatus*; or a strain of *Humicola*, preferably *Humicola lanuginosa*. The xylanase may preferably be an endo-1,4-beta-xylanase, more preferably an endo-1,4-beta-xylanase of GH10 or GH11. Examples of commercial xylanases include SHEARZYME™ and BIO-FEED WHEAT™ from Novozymes A/S, Denmark.

The hemicellulase may be added in an amount effective to hydrolyze hemicellulose, such as, in amounts from about 0.001 to 0.5 wt. % of total solids (TS), more preferably from about 0.05 to 0.5 wt. % of TS.

Xylanases may be added in amounts of 0.001-1.0 g/kg DM (dry matter) substrate, preferably in the amounts of 0.005-0.5 g/kg DM substrate, and most preferably from 0.05-0.10 g/kg DM substrate.

Xylose Isomerase

Xylose isomerases (D-xylose ketoisomerase) (E.C. 5.3.1.5.) are enzymes that catalyze the reversible isomerization reaction of D-xylose to D-xylulose. Some xylose isomerases also convert the reversible isomerization of D-glucose to D-fructose. Therefore, xylose isomarase is sometimes referred to as "glucose isomerase."

A xylose isomerase used in a method or process of the invention may be any enzyme having xylose isomerase activity and may be derived from any sources, preferably bacterial or fungal origin, such as filamentous fungi or yeast. Examples of bacterial xylose isomerases include the ones belonging to the genera *Streptomyces, Actinoplanes, Bacillus. Flavobacterium*, and *Thermotoga*, including *T. neapolitana* (Vieille et al., 1995, Appl. Environ. Microbiol. 61(5): 1867-1875) and *T. maritime*.

Examples of fungal xylose isomerases are derived species of *Basidiomycetes*.

A preferred xylose isomerase is derived from a strain of yeast genus *Candida*, preferably a strain of *Candida boidinii*, especially the *Candida boidinii* xylose isomerase disclosed by, e.g., Vongsuvanlert et al., 1988, Agric. Biol. Chem., 52(7). 1817-1824. The xylose isomerase may preferably be derived from a strain of *Candida boidinhi* (Kloeckera 2201), deposited as DSM 70034 and ATCC 48180, disclosed in Ogata et al., Agric. Biol. Chem., 33: 1519-1520 or Vongsuvanlen et al. 1988, Agric. Biol. Chem., 52(2): 1519-1520.

In one embodiment the xylose isomerase is derived from a strain of *Streptomyces*, e.g., derived from a strain of *Streptomyces murinus* (U.S. Pat. No. 4,687,742); *S. flavovirens, S. albus. S. achromogenus, S. echinatus, S. wedmorensis* all disclosed in U.S. Pat. No. 3,616,221. Other xylose isomerases are disclosed in U.S. Pat. Nos. 3,622,463, 4,351,903, 4,137,126, 3,625,828, HU patent no. 12,415, DE patent 2,417,642, JP patent no. 69,28,473, and WO 2004/044129 each incorporated by reference herein.

The xylose isomerase may be either in immobilized or liquid form. Liquid form is preferred.

Examples of commercially available xylose isomerases include SWEETZYME™ T from Novozymes A/S, Denmark.

The xylose isomerase is added to provide an activity level in the range from 0.01-100 IGIU per gram total solids.

Cellulolytic Enhancing Activity

The term "cellulolytic enhancing activity" is defined herein as a biological activity that enhances the hydrolysis of a lignocellulose derived material by proteins having cellulolytic activity. For purposes of the present invention, cellulolytic enhancing activity is determined by measuring the increase in reducing sugars or in the increase of the total of cellobiose and glucose from the hydrolysis of a lignocellulose derived material, e.g., pre-treated lignocellulose-containing material by cellulolytic protein under the following conditions. 1-50 mg of total protein/g of cellulose in PCS (pre-treated corn stover), wherein total protein is comprised of 80-99.5% w/w cellulolytic protein/g of cellulose in PCS and 0.5-20% w/w protein of cellulolytic enhancing activity for 1-7 day at 50° C. compared to a control hydrolysis with equal total protein loading without cellulolytic enhancing activity (1-50 mg of cellulolytic protein/g of cellulose in PCS).

The polypeptides having cellulolytic enhancing activity enhance the hydrolysis of a lignocellulose derived material catalyzed by proteins having cellulolytic activity by reducing the amount of cellulolytic enzyme required to reach the same degree of hydrolysis preferably at least 0.1-fold, more at least 0.2-fold, more preferably at least 0.3-fold, more preferably at least 0.4-fold, more preferably at least 0.5-fold, more preferably at least 1-fold, more preferably at least 3-fold, more preferably at least 4-fold, more preferably at least 5-fold, more preferably at least 10-fold, more preferably at least 20-fold, even more preferably at least 30-fold, most preferably at least 50-fold, and even most preferably at least 100-fold.

In a preferred embodiment the hydrolysis and/or fermentation is carried out in the presence of a cellulolytic enzyme in combination with a polypeptide having enhancing activity. In a preferred embodiment the polypeptide having enhancing activity is a family GH61A polypeptide. WO 2005/074647 discloses isolated polypeptides having cellulolytic enhancing activity and polynucleotides thereof from *Thielavia terrestris*. WO 2005/074656 discloses an isolated polypeptide having cellulolytic enhancing activity and a polynucleotide thereof from *Thermoascus aurantiacus*. U.S. Published Application Serial No. 2007/0077630 discloses an isolated polypeptide having cellulolytic enhancing activity and a polynucleotide thereof from *Trichoderma reesei*.

Proteases

A protease may be added during hydrolysis in step ii), fermentation in step iii) or simultaneous hydrolysis and fermentation. The protease may be any protease. In a preferred embodiment the protease is an acid protease of microbial origin, preferably of fungal or bacterial origin. An acid fungal protease is preferred, but also other proteases can be used.

Suitable proteases include microbial proteases, such as fungal and bacterial proteases. Preferred proteases are acidic proteases, i.e., proteases characterized by the ability to hydrolyze proteins under acidic conditions below pH 7.

Contemplated acid fungal proteases include fungal proteases derived from *Aspergillus, Mucor, Rhizopus, Candida, Corilus, Endothia, Enthomophtra, Irpex, Penicillium, Sclerotiumand Torulopsis*. Especially contemplated are proteases derived from *Aspergillus niger* (see, e.g., Koaze et al., 1964, Agr. Biol. Chem. Japan, 28: 216), *Aspergillus saitoi* (see, e.g., Yoshida, 1954, J. Agr. Chem. Soc. Japan, 28: 66), *Aspergillus awamori* (Hayashida et al., 1977, Agric. Biol. Chem., 42(5): 927-933, *Aspergillus* aculeatus (WO 95/02044), or *Aspergillus oryzae*, such as the pepA protease; and acidic proteases from *Mucor pusillus* or *Mucor miehei*.

Contemplated are also neutral or alkaline proteases, such as a protease derived from a strain of *Bacillus*. A particular protease contemplated for the invention is derived from *Bacillus amyloliquefaciens* and has the sequence obtainable at Swissprot as Accession No. P06832. Also contemplated are the proteases having at least 90% identity to amino acid sequence obtainable at Swissprot as Accession No. P06832 such as at least 92%, at least 95%, at least 96%, at least 97%, at least 98%, or particularly at least 99% identity.

Further contemplated are the proteases having at least 90% identity to amino acid sequence disclosed as SEQ.ID.NO:1 in the WO 2003/048353 such as at 92%, at least 95%, at least 96%, at least 97%, at least 98%, or particularly at least 99% identity.

Also contemplated are papain-like proteases such as proteases within EC 3.4.22.* (cysteine protease), such as EC 3.4.22.2 (papain), EC 3.4.22.6 (chymopapain), EC 3.4.22.7 (asclepain), EC 3.4.22.14 (actinidain). EC 3.4.22.15 (cathepsin L), EC 3.4.22.25 (glycyl endopeptidase) and EC 3.4.22.30 (caricain).

In an embodiment the protease is a protease preparation derived from a strain of *Aspergillus*, such as *Aspergillus oryzae*. In another embodiment the protease is derived from a strain of *Rhizomucor*, preferably *Rhizomucor meihei*. In another contemplated embodiment the protease is a protease preparation, preferably a mixture of a proteolytic preparation derived from a strain of *Aspergillus*, such as *Aspergillus oryzae*, and a protease derived from a strain of *Rhizomucor*, preferably *Rhizornucor meihei*.

Aspartic acid proteases are described in, for example, Handbook of Proteolytic Enzymes, Edited by A. J. Barrett, N. D. Rawlings and J. F. Woessner, Academic Press, San Diego, 1998, Chapter 270). Suitable examples of aspartic acid protease include, e.g., those disclosed in Berka et al., 1990. Gene, 96: 313); Berka et al., 1993, Gene, 125: 195-198; and Gomi et al., 1993, *Biosci. Biotech. Biochem.* 57: 1095-1100, which are hereby incorporated by reference.

Commercially available products include ALCALASE®, ESPERASET™, FLAVOURZYME™, PROMIX™, NEUTRASE®, RENNILASE®, NOVOZYM™ FM 2.01 L, and NOVOZYM™ 50006 (available from Novozymes A/S, Denmark) and GC106™ and SPEZYME™ FAN from Genencor Int., Inc., USA.

The protease may be present in an amount of 0.0001-1 mg enzyme protein per g DS, preferably 0.001 to 0.1 mg enzyme protein per g DS. Alternatively, the protease may be present in an amount of 0.0001 to 1 LAPU/g DS, preferably 0.001 to 0.1 LAPU/g DS and/or 0.0001 to 1 mAU-RH/g DS, preferably 0.001 to 0.1 mAU-RH/g DS.

Composition

In this aspect the invention relates to a composition comprising one or more pyrophosphatase enzymes. In a preferred embodiment the pyrophosphatase has inorganic pyrophosphatase activity (EC 3.6.1.1). Examples of suitable pyrophosphatase enzymes can be found the "Pyrophosphatase Enzymes" section above.

The composition may also comprise one or more carbohydrate-source generating enzymes, such as especially glucoamylases, beta-amylases, maltogenic amylases, pullulanases, alpha-glucosidases, or a mixture thereof.

In an embodiment the composition further comprises one or more other carbohydrases, such as alpha-amylases. In a preferred embodiment the alpha-amylase is an acid alpha-amylase or a fungal alpha-amylase, preferably an acid fungal alpha-amylase.

In an embodiment the composition comprises enzymes selected from the group consisting cellulolytic enzymes, such as cellulases, and/or hemicellulolytic enzymes, such as hemicellulases.

Examples of contemplated enzymes can be found in the "Enzymes" section above.

In another preferred embodiment the composition comprises one or more pyrophosphatase enzymes and further one or more fermenting organisms, such as yeast and/or bacteria. Examples of fermenting organisms can be found in the "Fermenting Organism" section above.

Use

In this aspect the invention relates to the use of pyrophosphatase enzyme for improving the fermentation product yield and/or fermentation rate during a fermentation process.

Transgenic Plant Material

In this aspect the invention relates to transgenic plant material transformed with one or more pyrophosphatase genes.

In one embodiment the invention relates to a transgenic plant, plant part, or plant cell which has been transformed with a polynucleotide sequence encoding a pyrophosphatase enzyme so as to express and produce the enzyme. The enzyme may be recovered from the plant or plant part, but in context of the present invention the plant or plant part containing the recombinant pyrophosphatase enzyme may be used in one or more of the processes of the invention concerned and described above.

The transgenic plant can be dicotyledonous (a dicot) or monocotyledonous (a Monocot). Examples of monocot plants are grasses, such as meadow grass (blue grass, *Poa*), forage grass such as *Festuca*, *Lolium*, temperate grass, such as *Agrostis*, and cereals, e.g., wheat, oats, rye, barley, rice, sorghum, and corn.

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, menstems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilisation of the invention are also considered plant parts, e.g., embryos, endosperms, aleurons and seeds coats.

Also included within the scope of the present invention are the progeny of such plants, plant parts, and plant cells.

The transgenic plant or plant cell expressing a pyrophosphatase enzyme may be constructed in accordance with methods well known in the art. In short, the plant or plant cell is constructed by incorporating one or more expression constructs encoding the pyrophosphatase into the plant host genome and propagating the resulting modified plant or plant cell into a transgenic plant or plant cell.

The expression construct is conveniently a nucleic acid construct which comprises a polynucleotide encoding pyrophosphosphatase enzyme operably linked with appropriate regulatory sequences required for expression of the polynucleotide sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the enzyme is desired to be expressed. For instance, the expression of the gene encoding a pyrophosphatase enzyme may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, and the rice actin 1 promoter may be used (Franck at al., 1980, *Cell* 21: 285-294, Christensen et al., 1992, *Plant at al., Biol.* 18: 675-689; Zhang at, 1991, *Plant Cell* 3: 1155-1165). Organ-specific promoters may be, for example, a promoter from storage sink tissues such as seeds, potato tubers, and fruits (Edwards & Coruzzi, 1990, *Ann. Rev, Genet.* 24: 275-303), or from metabolic sink tissues such as meristems (Ito et al., 1994, *Plant Mot Blot* 24: 863-878), a seed specific promoter such as the glutelin, prolamin, globulin, or albumin promoter from rice (Wu at al., 1998, *Plant and Cell Physiology* 39: 885-889), a Viola faba promoter from the legumin B4 and the unknown seed protein gene from Viola faba (Conrad at, 1998, *Journal of Plant Physiology* 152: 708-711), a promoter from a seed oil body protein (Chen at al., 1998, *Plant and Cell Physiology* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka at, 1993, *Plant Physiology* 102: 991-1000, the *chlorella* virus adenine methyltransferase gene promoter (Mitra and Higgins, 1994, *Plant Molecular Biology* 26: 85-93), or the aldP gene promoter from rice (Kagaya at al., 1995, *Molecular and General Genetics* 248: 668-674), or a wound inducible promoter such as the potato pin2 promoter (Xu et al., 1993, *Plant Molecular Biology* 22: 573-588). Likewise, the promoter may inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a pyrophosphatase in the plant. For instance, the promoter enhancer element may be an intron which is placed between the promoter and the polynucleotide sequence encoding a pyrophosphatase. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992. *Plant Molecular Biology* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275-281; Shimamoto, 1994, *Current Opinion Biotechnology* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21: 415-428.

Following transformation, the transformants having incorporated the expression construct are selected and regenerated into whole plants according to methods well-known in the art. Often the transformation procedure is designed for the selective elimination of selection genes either during regeneration or in the following generations by using, for example, co-transformation with two separate T-DNA constructs or site specific excision of the selection gene by a specific recombinase.

A method for producing a pyrophosphatase enzyme in a plant would comprise: (a) cultivating a transgenic plant or a plant cell comprising a polynucleotide encoding a pyrophosphatase enzyme under conditions conducive for production of the enzyme.

As mentioned above the transgenic plant material may be used in a process of the invention described above.

The transgenic plant is capable of expressing one or more pyrophosphatase enzymes in increased amounts compared to corresponding unmodified plant material.

Modified Fermenting Organism

In this aspect the invention relates to a modified fermenting organism transformed with a polynucleotide encoding a pyrophosphatase enzyme, wherein the fermenting organism is capable of expressing pyrophosphatase enzyme at fermentation conditions.

In a preferred embodiment the fermentation conditions are as defined according to the invention. In a preferred embodiment the fermenting organism is a microbial organism, such as yeast or filamentous fungus, or a bacterium. Examples of other fermenting organisms can be found the in "Fermenting Organisms" section.

A fermenting organism may be transformed with an pyrophosphatase encoding genes using techniques well know in the art.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure, including definitions will be controlling.

Various references are cited herein, the disclosures of which are incorporated by reference in their entireties.

Materials & Methods

Materials:

Pyrophosphatase from bakers yeast (*Saccharomyces cerevisiae*) was purchased from Sigma (I1643).

Pyrophosphatase from tobacco was purchased from Sigma (Product # P0414)

Pyrophosphatase from *E. coli* was purchased from Sigma (Product # I5907)

Pyrophosphatase from *Bacillus* was purchased from Sigma (Product # I2891)

Glucoamylase TC from *Trametes cingulata* disclosed in SEQ ID NO: 2 in WO 2006/069289 and available from Novozymes A/S, Denmark.

Glucoamylase (AMG A): Glucoamylase derived from *Trametes cingulate* disclosed in SEQ ID NO: 2 in WO 2006/069289 and available from Novozymes A/S.

Alpha-Amylase A (AA1): Hybrid alpha-amylase consisting of *Rhizomucor pusillus* alpha-amylase with *Aspergillus niger* glucoamylase linker and SBD disclosed as V039 in Table 5 in WO 2006/069290 (Novozymes A/S).

Cellulase preparation A: Cellulolytic composition comprising a polypeptide having cellulolytic enhancing activity (GH61A) disclosed in WO 2005/074656; a beta-glucosidase (fusion protein disclosed in WO 2008/057637) and cellulolytic enzymes preparation derived from *Trichoderma reesei*. Cellulase preparation A is disclosed in co-pending application PCT/US2008/065417.

Yeast: RED START™ available from Red Star/Lesaffre, USA RWB218 was received from Royal Nedalco/The Netherlands and is described in Kuyper et al., 2005, *FEMS Yeast Research* 5: 925-934.

Unwashed pre-treated corn stover (PCS). Acid-catalyzed, steam-exploded obtained from The National Renewable Energy Laboratory, Golden, Colo.

Methods:

Identity

The relatedness between two amino acid sequences or between two polynucleotide sequences is described by the parameter "identity".

For purposes of the present invention, the degree of identity between two amino acid sequences is determined by the Clustal method (Higgins, 1989, *CABIOS* 5: 151-153) using the LASERGENE™ MEGALIGN™ software (DNASTAR. Inc., Madison, Wis.) with an identity table and the following multiple alignment parameters: Gap penalty of 10 and gap length penalty of 10. Pairwise alignment parameters are Ktuple=1, gap penalty=3, windows=5, and diagonals=5.

For purposes of the present invention, the degree of identity between two polynucleotide sequences is determined by the Wilbur-Lipman method (Wilbur and Lipman, 1983, *Proceed-* ings of the National Academy of Science USA 80: 726-730) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=3, gap penalty=3, and windows=20.

Pyrophosphatase Activity Determination (PPase Assay)

*Sigma Unit Definition (Yeast)

One unit will liberate 1.0 micro mole of inorganic orthophosphate per min at pH 7.2 at 25° C.

*Sigma Unit Definition (Bacteria)

One unit will liberate 1.0 micro mole of inorganic orthophosphate per min at pH 9 at 25° C.

Above activity unit definitions are based on Unit definition from Sigma-Aldrich's PPase products: PPase from *Saccharomyces cerevisae* (product # I1643) and PPase from *Escerichia coli* (product # I5907).

*Sigma Unit Definition (Plant or Acid PPases)

One unit will release 1.0 nanomole of inorganic phosphate from 7-methyl-GTP in 30 min at pH 6.0 at 37° C. One 7-methyl-GTP unit (pH 6.0) is equivalent to 15 ATP units (pH 5.0).

Glucoamylase Activity

Glucoamylase activity may be measured in Glucoamylase Units (AGU).

Glucoamylase Activity (AGU)

The Novo Glucoamylase Unit (AGU) is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

| AMG incubation: | |
| --- | --- |
| Substrate: | maltose 23.2 mM |
| Buffer: | acetate 0.1M |
| pH: | 4.30 ± 0.05 |
| Incubation temperature: | 37° C. ± 1 |
| Reaction time: | 5 minutes |
| Enzyme working range: | 0.5-4.0 AGU/mL |

| Color reaction: | |
| --- | --- |
| GlucDH: | 430 U/L |
| Mutarotase: | 9 U/L |
| NAD: | 0.21 mM |
| Buffer: | phosphate 0.12M; 0.15M NaCl |
| pH: | 7.60 ± 0.05 |
| Incubation temperature: | 37° C. ± 1 |
| Reaction time: | 5 minutes |
| Wavelength: | 340 nm |

A folder (EB-SM-0131.02/01) describing this analytical method in more detail is available on request from Novozymes A/S, Denmark, which folder is hereby included by reference.

Alpha-Amylase Activity (KNU)

The alpha-amylase activity may be determined using potato starch as substrate. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard.

One Kilo Novo alpha amylase Unit (KNU) is defined as the amount of enzyme which, under standard conditions (i.e., at 37° C. +/− 0.05: 0.0003 M $Ca^{2+}$; and pH 5.6) dextrinizes 5260 mg starch dry substance Merck Amylum solubile.

A folder EB-SM-0009.02/01 describing this analytical method in more detail is available upon request to Novozymes A/S, Denmark, which folder is hereby included by reference.

Acid Alpha-Amylase Activity (AFAU)

When used according to the present invention the activity of an acid alpha-amylase may be measured in AFAU (Acid Fungal Alpha-amylase Units). Alternatively, activity of acid alpha-amylase may be measured in AAU (Acid Alpha-amylase Units).

Acid Alpha-Amylase Units (AAU)

The acid alpha-amylase activity can be measured in AAU (Acid Alpha-amylase Units), which is an absolute method. One Acid Amylase Unit (AAU) is the quantity of enzyme converting 1 g of starch (100% of dry matter) per hour under standardized conditions into a product having a transmission at 620 nm after reaction with an iodine solution of known strength equal to the one of a color reference.

| Standard conditions/reaction conditions: | |
| --- | --- |
| Substrate: | Soluble starch. Concentration approx. 20 g DS/L. |
| Buffer: | Citrate, approx. 0.13M, pH = 4.2 |
| Iodine solution: | 40.176 g potassium iodide + 0.088 g iodine/L |
| City water | 15°-20° dH (German degree hardness) |
| pH: | 4.2 |
| Incubation temperature: | 30° C. |
| Reaction time: | 11 minutes |
| Wavelength: | 620 nm |
| Enzyme concentration: | 0.13-0.19 AAU/mL |
| Enzyme working range: | 0.13-0.19 AAU/mL |

The starch should be Lintner starch, which is a thin-boiling starch used in the laboratory as colorimetric indicator. Lintner starch is obtained by dilute hydrochloric acid treatment of native starch so that it retains the ability to color blue with iodine. Further details can be found in EP 0140410 B2, which disclosure is hereby included by reference.

Determination of FAU-F

FAU-F Fungal Alpha-Amylase Units (Fungamyl) is measured relative to an enzyme standard of a declared strength.

| Reaction conditions | |
| --- | --- |
| Temperature | 37° C. |
| pH | 7.15 |
| Wavelength | 405 nm |
| Reaction time | 5 min |
| Measuring time | 2 min |

A folder (EB-SM-0216.02) describing this standard method in more detail is available on request from Novozymes A/S, Denmark, which folder is hereby included by reference.

Acid Alpha-Amylase Activity (AFAU)

Acid alpha-amylase activity may be measured in AFAU (Acid Fungal Alpha-amylase Units), which are determined relative to an enzyme standard. 1 AFAU is defined as the amount of enzyme which degrades 5.260 mg starch dry matter per hour under the below mentioned standard conditions.

Acid alpha-amylase, an endo-alpha-amylase (1,4-alpha-D-glucan-glucanohydrolase, E.C. 3.2.1.1) hydrolyzes alpha-1,4-glucosidic bonds in the inner regions of the starch molecule to form dextrins and oligosaccharides with different chain lengths. The intensity of color formed with iodine is directly proportional to the concentration of starch. Amylase activity is determined using reverse colorimetry as a reduction in the concentration of starch under the specified analytical conditions,

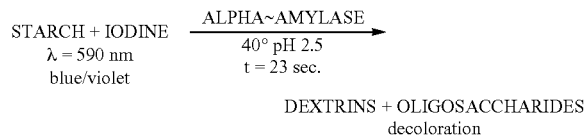

| Standard conditions/reaction conditions: | |
|---|---|
| Substrate: | Soluble starch, approx. 0.17 g/L |
| Buffer: | Citrate, approx. 0.03M |
| Iodine (I2): | 0.03 g/L |
| CaCl$_2$: | 1.85 mM |
| pH: | 2.50 ± 0.05 |
| Incubation temperature: | 40° C. |
| Reaction time: | 23 seconds |
| Wavelength: | 590 nm |
| Enzyme concentration: | 0.025 AFAU/mL |
| Enzyme working range: | 0.01-0.04 AFAU/mL |

A folder EB-SM-0259.02/01 describing this analytical method in more detail is available upon request to Novozymes AIS, Denmark, which folder is hereby included by reference.

Measurement of Cellulase Activity Using Filter Paper Assay (FPU Assay)

1. Source of Method
1.1 The method is disclosed in a document entitled "Measurement of Cellulase Activities" by Adney, B. and Baker, J., 1996, Laboratory Analytical Procedure, LAP-006, National Renewable Energy Laboratory (NREL), It is based on the IUPAC method for measuring cellulase activity (Grose, T. K., 1987, Measurement of Cellulase Activities, Pure & Appl. Chem. 59: 257-268.
2. Procedure
2.1 The method is carried out as described by Adney and Baker. 1996, supra, except for the use of a 96 well plates to read the absorbance values after color development, as described below.
2.2 Enzyme Assay Tubes:
2.2.1 A rolled filter paper strip (#1 Whatman; 1×6 cm; 50 mg) is added to the bottom of a test tube (13×100 mm),
2.2.2 To the tube is added 1.0 mL of 0.05 M Na-citrate buffer (pH 4.80),
2.2.3 The tubes containing filter paper and buffer are incubated 5 min. at 50° C. (+0.1° C.) in a circulating water bath.
2.2.4 Following incubation, 0.5 mL of enzyme dilution in citrate buffer is added to the tube. Enzyme dilutions are designed to produce values slightly above and below the target value of 2.0 mg glucose.
2.2.5 The tube contents are mixed by gently vortexing for 3 seconds.
2.2.6 After vortexing, the tubes are incubated for 60 mins. at 50° C. (±0.1° C.) in a circulating water bath.
2.2.7 Immediately following the 60 min. incubation, the tubes are removed from the water bath, and 3.0 mL of DNS reagent is added to each tube to stop the reaction. The tubes are vortexed 3 seconds to mix.
2.3 Blank and Controls
2.3.1 A reagent blank is prepared by adding 1.5 mL of citrate buffer to a test tube.
2.3.2 A substrate control is prepared by placing a rolled filter paper strip into the bottom of a test tube, and adding 1.5 mL of citrate buffer.
2.3.3 Enzyme controls are prepared for each enzyme dilution by mixing 1.0 mL of citrate buffer with 0.5 mL of the appropriate enzyme dilution.
2.3.4 The reagent blank, substrate control, and enzyme controls are assayed in the same manner as the enzyme assay tubes, and done along with them.
2.4 Glucose Standards
2.4.1 A 100 mL stock solution of glucose (10.0 mg/mL) is prepared, and 5 mL aliquots are frozen. Prior to use: aliquots are thawed and vortexed to mix.
2.4.2 Dilutions of the stock solution are made in citrate buffer as follows:
G1=1.0 mL stock+0.5 mL buffer=6.7 mg/mL=3.3 mg/0.5 mL
G2=0.75 mL stock+0.75 mL buffer=5.0 mg/mL=2.5 mg/0.5 mL
G3=0.5 mL stock+1.0 mL buffer=3.3 mg/mL=1.7 mg/0.5 mL
G4=0.2 mL stock+0.8 mL buffer=2.0 mg/mL=1.0 mg/0.5 mL
2.4.3 Glucose standard tubes are prepared by adding 0.5 mL of each dilution to 1.0 mL of citrate buffer.
2.4.4 The glucose standard tubes are assayed in the same manner as the enzyme assay tubes, and done along with them.
2.5 Color Development
2.5.1 Following the 60 min. incubation and addition of DNS the tubes are all boiled together for 5 mins. in a water bath.
2.5.2 After boiling, they are immediately cooled in an ice/water bath.
2.5.3 When cool, the tubes are briefly vortexed, and the pulp is allowed to settle. Then each tube is diluted by adding 50 microL from the tube to 200 microL of ddH$_2$O in a 96-well plate. Each well is mixed, and the absorbance is read at 540 nm.
2.6 Calculations (examples are given in the NREL document)
2.6.1 A glucose standard curve is prepared by graphing glucose concentration (mg/0.5 mL) for the four standards (G1-G4) vs. $A_{540}$. This is fitted using a linear regression (Prism Software), and the equation for the line is used to determine the glucose produced for each of the enzyme assay tubes.
2.6.2 A plot of glucose produced (mg/0.5 mL) vs. total enzyme dilution is prepared, with the Y-axis (enzyme dilution) being on a log scale.
2.6.3 A line is drawn between the enzyme dilution that produced just above 2.0 mg glucose and the dilution that produced just below that. From this line, it is determined the enzyme dilution that would have produced exactly 2.0 mg of glucose.
2.6.4 The Filter Paper Units/mL (FPU/mL) are calculated as follows:
FPU/mL=0.37/enzyme dilution producing 2.0 mg glucose.

Protease Assay Method—AU(RH)

The proteolytic activity may be determined with denatured hemoglobin as substrate. In the Anson-Hemoglobin method for the determination of proteolytic activity denatured hemoglobin is digested, and the undigested hemoglobin is precipitated with trichloroacetic acid (TCA). The amount of TCA soluble product is determined with phenol reagent, which gives a blue color with tyrosine and tryptophan.

One Anson Unit (AU-RH) is defined as the amount of enzyme which under standard conditions (i.e., 25° C., pH 5.5 and 10 min. reaction time) digests hemoglobin at an initial rate such that there is liberated per minute an amount of TCA soluble product which gives the same color with phenol reagent as one milliequivalent of tyrosine.

The AU(RH) method is described in EAL-SM-0350 and is available from Novozymes A/S Denmark on request.

Protease assay method (LAPU)

1 Leucine Amino Peptidase Unit (LAPU) is the amount of enzyme which decomposes 1 microM substrate per minute at the following conditions: 26 mM of L-leucine-p-nitroanilide as substrate, 0.1 M Tris buffer (pH 8.0), 37° C., 10 minutes reaction time.

LAPU is described in EB-SM-0298,02/01 available from Novozymes A/S Denmark on request.

Determination of Maltogenic Amylase Activity (MANU)

One MANU (Maltogenic Amylase Novo Unit) may be defined as the amount of enzyme required to release one micro mole of maltose per minute at a concentration of 10 mg of maltotriose (Sigma M 8378) substrate per ml of 0.1 M citrate buffer, pH 5.0 at 37° C. for 30 minutes.

EXAMPLES

Example 1

Figure 2:
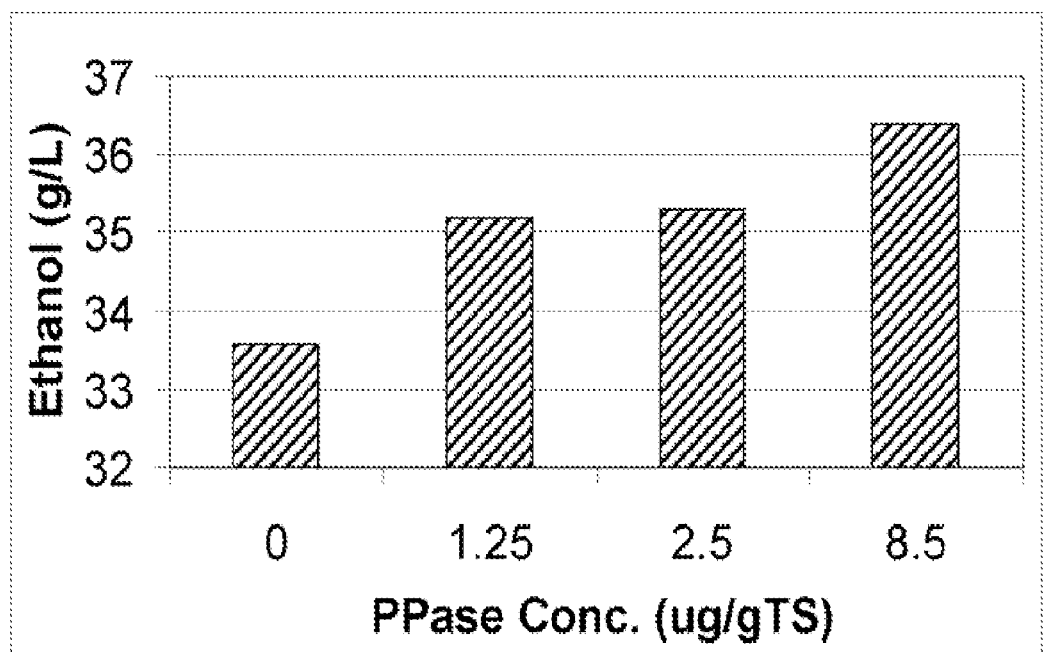
FIG. 2. Effect of pyrophosphatase on ethanol production after 48 hour fermentation of PCS hydrolysates.

Effect of Pyrophosphatase (PPase) in the Fermentation of Pretreated Corn Stover (PCS) Hydrolysates to Produce Ethanol All treatments were evaluated via mini-scale fermentations. NREL dilute acid steam exploded corn stover (PCS) was diluted with water and adjusted to pH 5.0 with NH$_4$OH. Penicillin and citrate buffer and YP (yeast extract and peptone) medium were also added prior to the hydrolysis. The total solids (TS) level was 20%. The sample was then hydrolyzed for 72 hours at 50° C. with an effective amount of Cellulase Preparation A. Following the hydrolysis step, the sample was sterile-filtered to remove the solids and the filtrate was used for fermentation, Fermentation was carried on in 40 ml mini vials at 30° C. Each vial contained 5.0 ml PCS hydrolysates and 4.75 ml YPDX (yeast extract, peptone, glucose and xylose) medium. Each vial was dosed with the appropriate amount of bakers yeast PPase based on the dosage shown in the table below, followed by inoculation of 0.25 ml over-night RWB218 propagate. After inoculation, the vials were incubated in the 30° C. shaker at 150 rpm. All tests were conducted in triplicate. Samples were taken during the fermentation and at the end of fermentation (48 hours) to measure the ethanol (FIG. 2), glucose (FIG. 1*a*), xylose (FIG. 1*b*), acetic acid and glycerol levels by HPLC. The HPLC preparation consisted of stopping the reaction by addition of 40% H$_2$SO$_4$ (1% v/v addition), centrifuging, and filtering through a 0.20 micrometer filter. Samples were stored at 4° C. until analysis. Agilent™ 1100 HPLC system coupled with RI detector was used. The separation column was aminex HPX-87H ion exclusion column (300 mm×7.8 mm) from Bio-Rad™.

| Treatments | PPase dose (ug/gTS) |
|---|---|
| 1 Control | |
| 2 PPase | 1.25 |
| 3 PPase | 2.5 |
| 4 PPase | 8.5 |

Example 2

Figure 3:
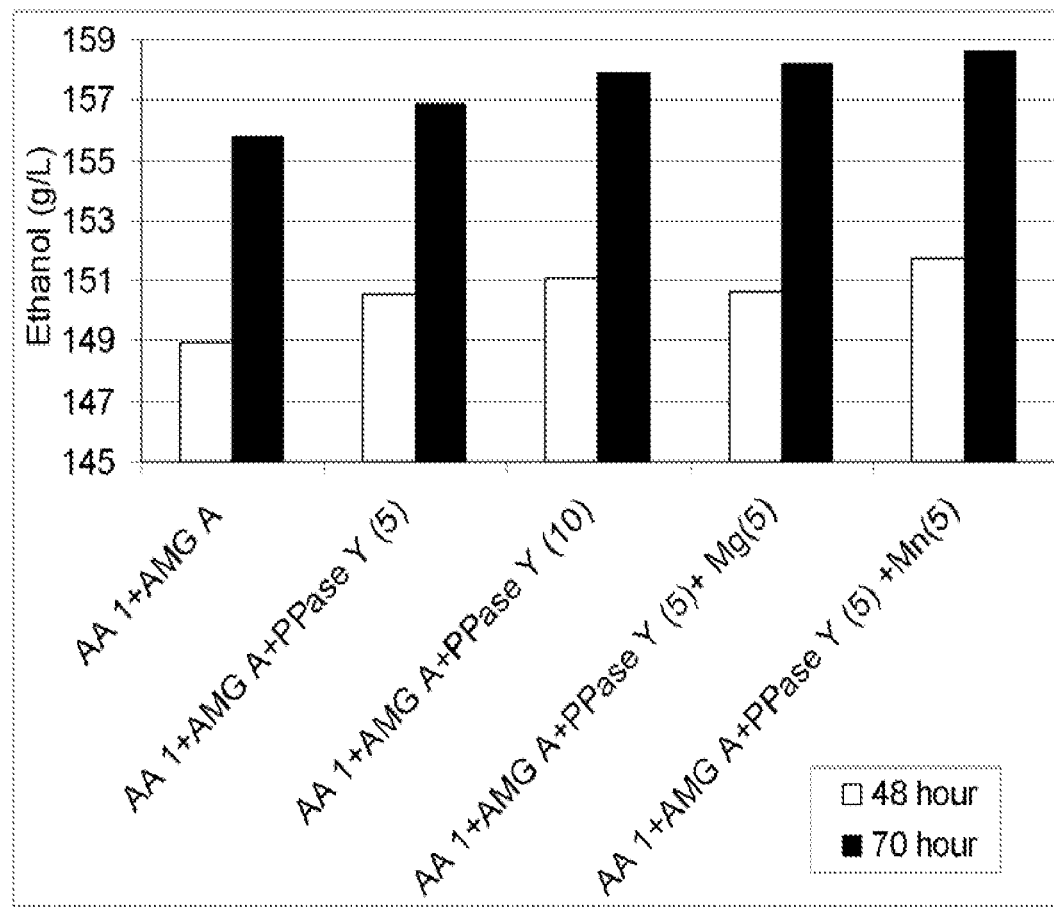
FIG. 3. Effect of bakers yeast pyrophosphatase, with or without magnesium or manganese metal ion on ethanol yield in an SSF process.
Figure 4:
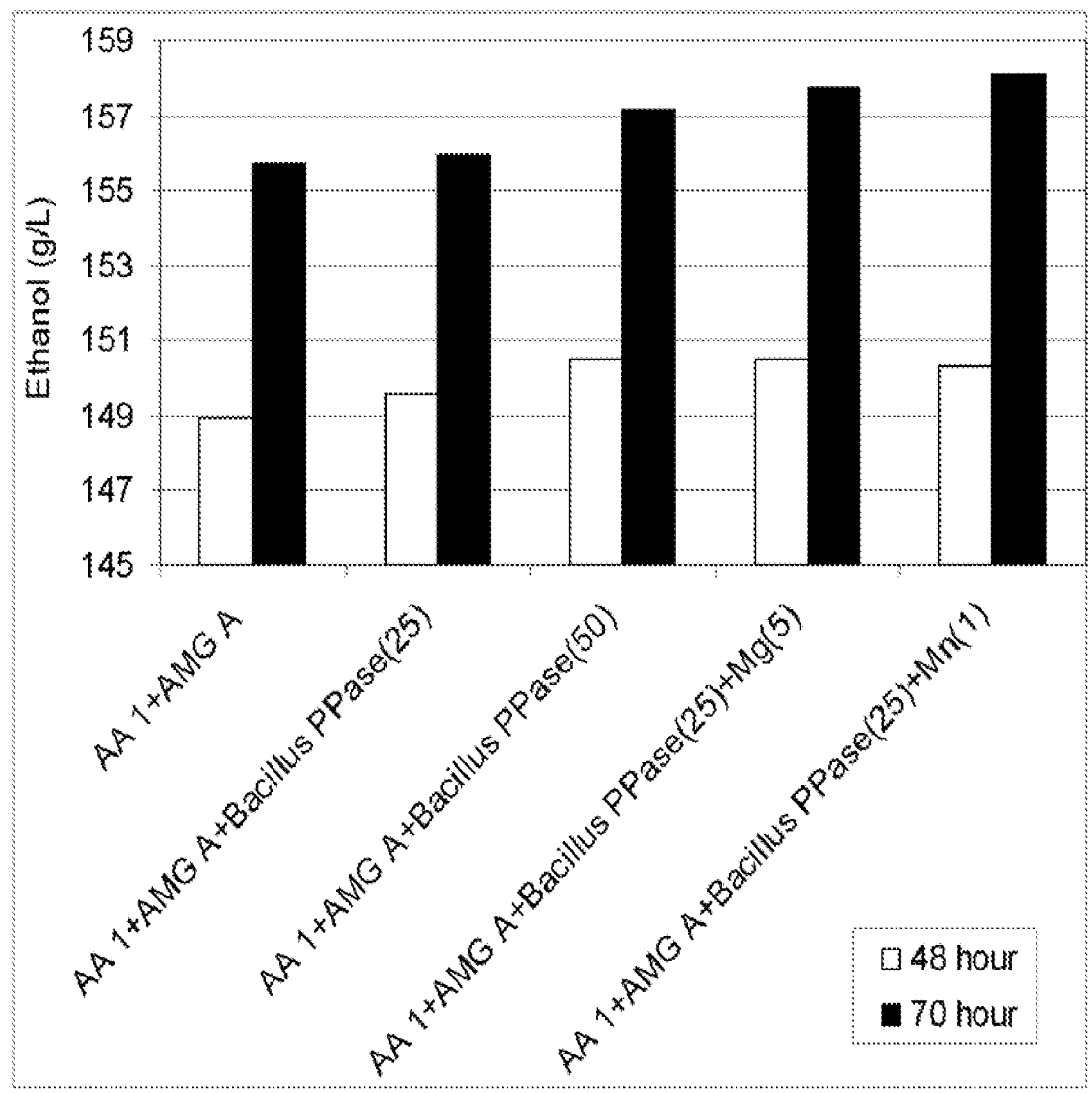
FIG. 4. Effect of *Bacillus* pyrophosphatase, with or without magnesium or manganese metal ion on ethanol yield in an SSF process.
Figure 5:
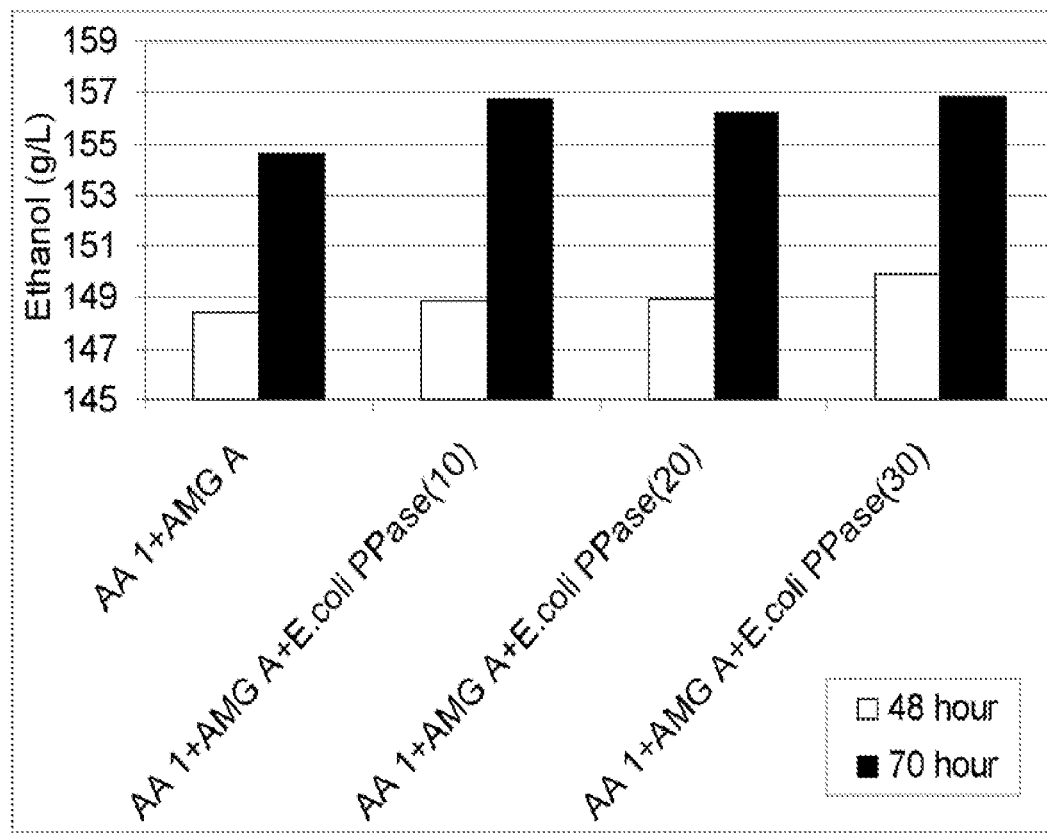
FIG. 5. Effect of *E. coli* pyrophosphatase on ethanol yield in an SSF process.
Figure 6:
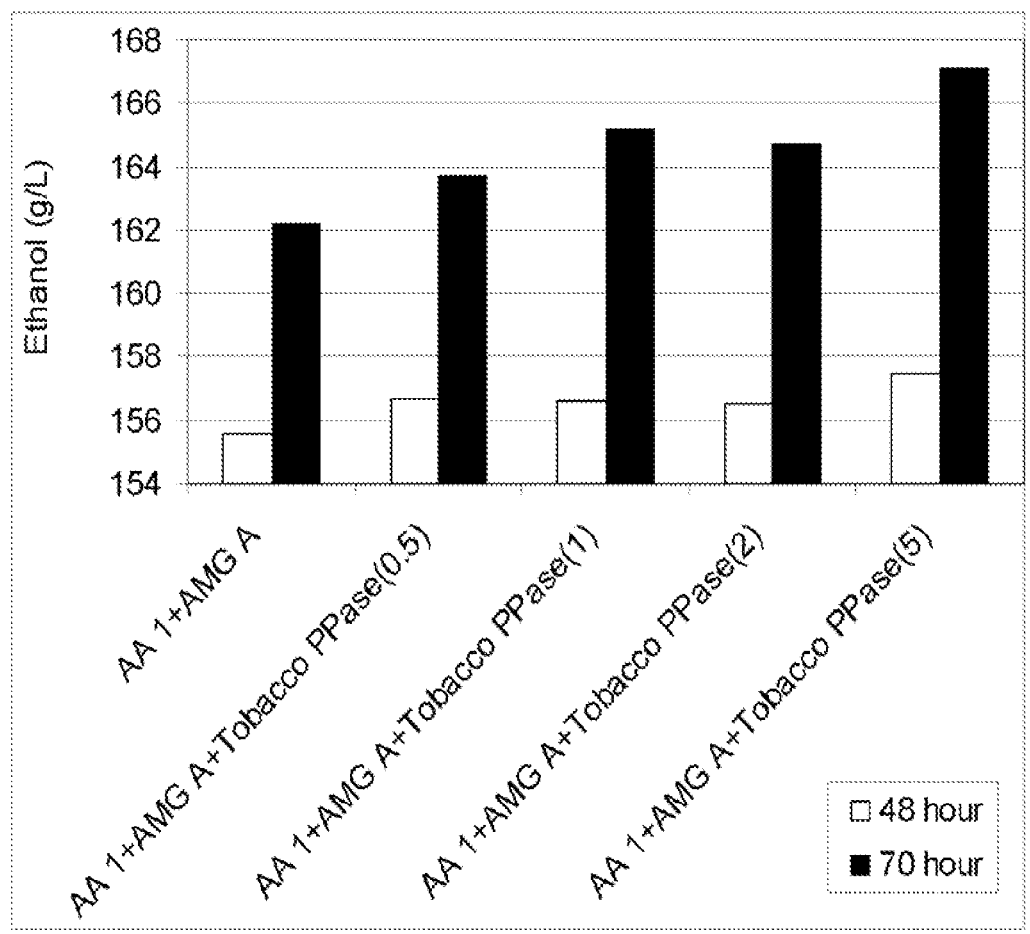
FIG. 6. Effect of tobacco pyrophosphatase on ethanol yield in an SSF process.

Effect of Pyrophosphatase (PPase) Toward Combination of Alpha-Amylase (AA 1) and Glucoamylase (AMG A) in One-Step Simultaneous Saccharification and Fermentation (SSF) Process All treatments were evaluated via mini-scale fermentations. 410 g of ground yellow dent corn (with an average particle size around 0.5 mm) was added to 590 g tap water. This mixture was supplemented with 3.0 ml 1 g/L penicillin and 1 g of urea. The pH of this slurry was adjusted to 4.5 with 40% H$_2$SO$_4$. Dry solid (DS) level was determined to be around 35 wt. %. Approximately 5 g of this slurry was added to 20 ml vials. Each vial was dosed with the appropriate amount of enzyme dosage shown in table below followed by addition of 200 micro liters yeast propagate/5 g slurry. Actual enzyme dosages were based on the exact weight of corn slurry in each vial. Vials were incubated at 32° C. Nine replicate fermentations of each treatment were run. Three replicates were selected for 24 hours, 48 hours and 70 hours time point analysis. Vials were vortexed at 24, 48 and 70 hours and analyzed by HPLC. The HPLC preparation consisted of stopping the reaction by addition of 50 micro liters of 40% H$_2$SO$_4$, centrifuging, and filtering through a 0.45 micrometer filter. Samples were stored at 4° C. until analysis. Agilent™ 1100 HPLC system coupled with RI detector was used to determine ethanol and oligosaccharides concentration. The separation column was aminex HPX-87H ion exclusion column (300 mm×7.8 mm) from BioRad™. The results for Experiment 1 are summarized in FIGS. 3 and 4, and the results for Experiments 2 and 3 are summarized in FIGS. 5 and 6, respectively.

Experiment 1

| Treatments | AA 1 (FAU-F/gDS) | AMG A (AGU/g DS) | PPase (micro gram protein/ gDS) | Metal ion (mM/ gDS) |
|---|---|---|---|---|
| 1 AA 1 + AMG A | 0.0475 | 0.50 | | |
| 2 AA 1 + AMG A + Yeast PPase | 0.0475 | 0.50 | 5 | |
| 3 AA 1 + AMG A + Yeast PPase | 0.0475 | 0.50 | 10 | |
| 4 AA 1 + AMG A + *Bacillus* PPase | 0.0475 | 0.50 | 25 | |
| 5 AA 1 + AMG A + *Bacillus* PPase | 0.0475 | 0.50 | 50 | |
| 6 AA 1 + AMG A + Yeast PPase + Magnesium | 0.0475 | 0.50 | 5 | 5 |
| 7 AA 1 + AMG A + Yeast PPase + Manganese | 0.0475 | 0.50 | 5 | 5 |
| 8 AA 1 + AMG A + *Bacillus* PPase + Magnesium | 0.0475 | 0.50 | 25 | 5 |
| 9 AA 1 + AMG A + *Bacillus* PPase + Manganese | 0.0475 | 0.50 | 25 | 1 |

Experiment 2

| Treatments | AA 1 (FAU-F/gDS) | AMG A (AGU/g DS) | PPase (mg solids/ gDS) |
|---|---|---|---|
| 1 AA 1 + AMG A | 0.0475 | 0.50 | |
| 2 AA 1 + AMG A + *E. coli* PPase | 0.0475 | 0.50 | 10 |
| 3 AA 1 + AMG A + *E. coli* PPase | 0.0475 | 0.50 | 20 |
| 4 AA 1 + AMG A + *E. coli* PPase | 0.0475 | 0.50 | 30 |

Experiment 3

| Treatments | AA 1 (FAU-F/gDS) | AMG A (AGU/g DS) | PPase (units/gDS) |
|---|---|---|---|
| 1 AA 1 + AMG A | 0.0475 | 0.50 | |
| 2 AA 1 + AMG A + Tobacco PPase | 0.0475 | 0.50 | 0.5 |
| 3 AA 1 + AMG A + Tobacco PPase | 0.0475 | 0.50 | 1 |
| 4 AA 1 + AMG A + Tobacco PPase | 0.0475 | 0.50 | 2 |
| 5 AA 1 + AMG A + Tobacco PPase | 0.0475 | 0.50 | 5 |

The invention claimed is:

1. A process of fermenting plant material into a fermentation product in a fermentation medium using a fermenting organism, wherein one or more exogenous pyrophosphatase enzymes are present in the fermentation medium.

2. The process of claim 1, wherein a metal ion is present or added during fermentation.

3. The process of claim 2, wherein the metal ion is selected from the group consisting of $Mg^{2+}$, $Mn^{2+}$, and $Zn^{2+}$, or a combination of two or more thereof.

4. The process of claim 1, wherein a carbohydrate-source generating enzyme is present during fermentation.

5. The process of claim 4, wherein the carbohydrate-source generating enzyme is selected from the group consisting of glucoamylase, β-amylase, maltogenic amylase, pullulanase, α-glucosidase, or a mixture of two or more thereof.

6. The process of claim 1, wherein an acid fungal α-amylase is present during fermentation.

7. The process of claim 1, wherein the fermenting organism is yeast, filamentous fungus, or bacteria.

8. A process of producing a fermentation product from starch-containing material comprising the steps of:
   i) liquefying starch-containing material;
   ii) saccharifying the liquefied material;
   iii) fermenting with one or more fermenting organisms;
   wherein the fermentation is carried out as defined in claim 1.

9. The process of claim 8, further comprising, prior to the step i), the steps of:
   x) reducing the particle size of starch-containing material by milling; and
   y) forming a slurry comprising the starch-containing material and water.

10. The process of producing a fermentation product from starch-containing material, comprising the steps of:
    (a) saccharifying starch-containing material at a temperature below the initial gelatinization temperature of said starch-containing material,
    (b) fermenting using a fermenting organism, wherein fermentation is carried out as defined in claim 1.

11. The process of claim 8, wherein the starch-containing material is selected from the group consisting of corn, cassava, wheat, barley, rye, milo, and potatoes, or any combination thereof.

12. The process of producing a fermentation product from lignocellulose-containing material, comprising the steps of:
    (a) pre-treating lignocellulose-containing material;
    (b) hydrolyzing the material;
    (c) fermenting with a fermenting organism;
    wherein fermentation is carried out as defined in claim 1.

13. The process of claim 12, wherein the lignocellulose-containing material originates from materials selected from the group consisting of corn stover, corn cobs, corn fiber, hardwood, softwood, cereal straw, wheat straw, switchgrass, rice hulls, Miscanthus, municipal solid waste, industrial organic waste, bagasse, and office paper, or mixtures thereof.

14. The process of claim 13, wherein the fermenting organism is a C6 or C5 fermenting organism.

15. The process of claim 1, wherein the fermenting organism is a yeast.

16. The process of claim 1, wherein the fermentation product is ethanol.

17. The process of claim 16, wherein the fermentation product is recovered after fermentation by distillation.

* * * * *